United States Patent
Tanaka

(10) Patent No.: US 9,028,434 B2
(45) Date of Patent: *May 12, 2015

(54) ULTRASOUND OPERATION APPARATUS, CAVITATION CONTROL METHOD, AND ULTRASOUND TRANSDUCER CONTROL METHOD

(75) Inventor: Kazue Tanaka, Sagamihara (JP)

(73) Assignee: Olympus Medical Systems Corp., Tokyo (JP)

( * ) Notice: Subject to any disclaimer, the term of this patent is extended or adjusted under 35 U.S.C. 154(b) by 541 days.

This patent is subject to a terminal disclaimer.

(21) Appl. No.: 12/467,572

(22) Filed: May 18, 2009

(65) Prior Publication Data

US 2010/0292573 A1  Nov. 18, 2010

(51) Int. Cl.
| | |
|---|---|
| *A61N 7/00* | (2006.01) |
| *B06B 1/02* | (2006.01) |
| *A61B 17/32* | (2006.01) |
| *A61B 18/14* | (2006.01) |
| *A61B 17/00* | (2006.01) |
| *A61B 17/22* | (2006.01) |
| *A61B 19/00* | (2006.01) |

(52) U.S. Cl.
CPC ....... *B06B 1/0253* (2013.01); *A61B 17/320092* (2013.01); *A61B 18/1442* (2013.01); *A61B 2017/00017* (2013.01); *A61B 2017/00026* (2013.01); *A61B 2017/00039* (2013.01); *A61B 2017/22009* (2013.01); *A61B 2019/448* (2013.01); *A61B 2019/4857* (2013.01)

(58) Field of Classification Search
CPC .................................. A61N 7/00; A61N 7/02
USPC .............................................. 601/2; 600/439
See application file for complete search history.

(56) References Cited

U.S. PATENT DOCUMENTS

| | | | |
|---|---|---|---|
| 6,708,420 B1 * | 3/2004 | Flanagan ........................ 33/556 |
| 6,761,690 B2 | 7/2004 | Sakurai et al. |
| 2001/0039389 A1 | 11/2001 | Sakurai et al. |

(Continued)

FOREIGN PATENT DOCUMENTS

| | | |
|---|---|---|
| CN | 101084072 A | 12/2007 |
| GB | 2 416 458 A | 1/2006 |

(Continued)

OTHER PUBLICATIONS

Abstract of International PCT Publication No. WO 00/53263, dated Sep. 14, 2000.

(Continued)

*Primary Examiner* — Tse Chen
*Assistant Examiner* — Hien Nguyen
(74) *Attorney, Agent, or Firm* — Scully, Scott, Murphy & Presser, P.C.

(57) ABSTRACT

An ultrasound operation apparatus comprises: an ultrasound transducer; a driving section that drives the ultrasound transducer by a drive signal; a probe having a proximal end section provided with the ultrasound transducer and a distal end section to which ultrasound oscillation is transmitted, the probe performing a treatment on a living tissue using ultrasound oscillation at the distal end section; a detecting section that detects, from a drive signal, a physical quantity which varies due to cavitation generated by ultrasound oscillation of the distal end section; and an output control section that controls an output of the driving section in accordance with the detected physical quantity.

11 Claims, 21 Drawing Sheets

(56) References Cited

U.S. PATENT DOCUMENTS

| | | | |
|---|---|---|---|
| 2003/0056568 A1* | 3/2003 | Kleinberg et al. | 73/19.01 |
| 2003/0221561 A1* | 12/2003 | Milo | 96/175 |
| 2004/0162509 A1 | 8/2004 | Sakurai et al. | |
| 2005/0113690 A1* | 5/2005 | Halmann et al. | 600/437 |
| 2008/0316865 A1* | 12/2008 | Young et al. | 367/140 |
| 2010/0106019 A1* | 4/2010 | Friemel et al. | 600/439 |

FOREIGN PATENT DOCUMENTS

| | | |
|---|---|---|
| JP | 2001-212514 | 8/2001 |
| JP | 2001-346805 | 12/2001 |
| JP | 2002-537955 | 11/2002 |
| JP | 3754113 | 12/2005 |
| JP | 2006-130313 | 5/2006 |
| JP | 2008-055151 | 3/2008 |
| JP | 2008-506527 A | 3/2008 |
| JP | 2008-188160 | 8/2008 |
| WO | WO 2005/094701 A1 | 10/2005 |
| WO | WO 2006/008502 A2 | 1/2006 |

OTHER PUBLICATIONS

Abstract of Japanese Patent Application Laid-Open Publication No. 08-131454, dated May 28, 1996.

\* cited by examiner

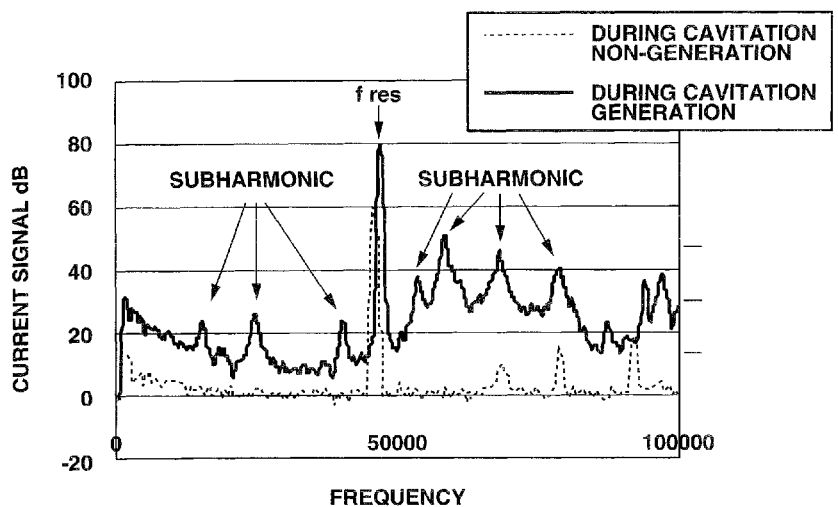
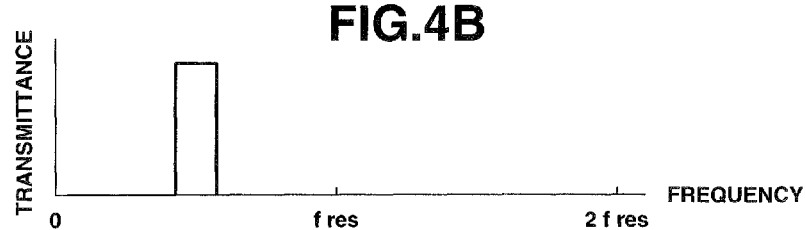
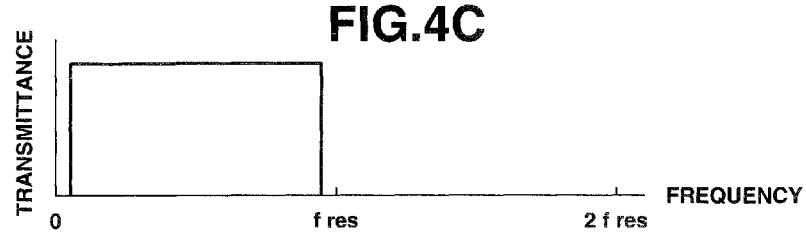
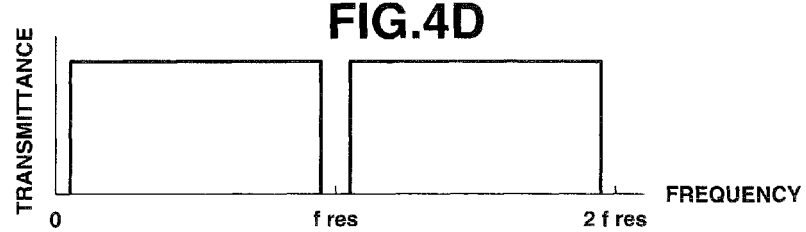

ULTRASOUND OPERATION APPARATUS, CAVITATION CONTROL METHOD, AND ULTRASOUND TRANSDUCER CONTROL METHOD

BACKGROUND OF THE INVENTION

1. Field of the Invention

The present invention relates to an ultrasound operation apparatus that performs operations using ultrasound oscillation and controls cavitation generated in accompaniment with ultrasound oscillation, a cavitation control method, and an ultrasound transducer control method.

2. Description of Related Art

In recent years, ultrasound operation apparatuses that perform operations on living tissues using ultrasound oscillation generated by an ultrasound transducer have been widely used. When ultrasound oscillation is applied to living tissues, cavitation may occur due to liquids contained in living tissue. The cavitation is the generation of vapor bubbles caused by liquid evaporation when the pressure of a liquid falls below a vapor pressure determined by the temperature of the liquid.

Accordingly, when compression waves are generated using ultrasound oscillation, the generation of negative pressure causes cavitation.

In this light, for example, in Japanese Patent Application Laid-Open Publication No. 2002-537955, an apparatus is disclosed in which therapeutic ultrasound is irradiated to a position inside a body while a cavitation level is monitored using a hydrophone.

In addition, International Publication No. WO2005/094701 discloses an apparatus provided with a sound pressure signal receiving probe on an ultrasound irradiating piezoelectric element, which controls ultrasound irradiating conditions using the sound pressure signal receiving probe according to a sound pressure signal emitted from cavitation bubbles.

SUMMARY OF THE INVENTION

An ultrasound operation apparatus according to an embodiment of the present invention includes: an ultrasound transducer capable of generating ultrasound oscillation; a driving section that drives the ultrasound transducer by a drive signal; a probe having a proximal end section operatively coupled to the ultrasound transducer and a distal end section that generates ultrasound oscillation for treating a living tissue, the probe transmitting the ultrasound oscillation generated by the ultrasound transducer from the proximal end section to the distal end section; a detecting section that detects a physical quantity which varies due to cavitation generated by ultrasound oscillation of the distal end section of the probe from the drive signal applied to the ultrasound transducer; and an output control section that controls an output of the driving section so as to vary the ultrasound oscillation of the probe in accordance with the physical quantity detected by the detecting section.

An ultrasound operation apparatus according to one aspect of the present invention includes: an ultrasound transducer capable of generating ultrasound oscillation; a driving section that drives the ultrasound transducer by a drive signal; a probe having a proximal end section operatively coupled to the ultrasound transducer and a distal end section that generates ultrasound oscillation for treating a living tissue, the probe transmitting the ultrasound oscillation generated by the ultrasound transducer from the proximal end section to the distal end section; a resonant frequency tracking section that automatically adjusts a frequency of the drive signal so as to track a resonant frequency of the ultrasound transducer and causes the distal end section to ultrasound-oscillate at the resonant frequency; a detecting section that detects cavitation by detecting from the drive signal a frequency component signal having a frequency component excluding the resonant frequency; and an output control section that performs control so as to vary an output of the drive signal that drives the ultrasound transducer in accordance with a detection result of the detecting section.

An ultrasound operation apparatus according to one aspect of the present invention includes: an ultrasound transducer capable of generating ultrasound oscillation; a driving section that drives the ultrasound transducer by a drive signal; a probe having a proximal end section operatively coupled to the ultrasound transducer and a distal end section that generates ultrasound oscillation for treating a living tissue, the probe transmitting the ultrasound oscillation generated by the ultrasound transducer from the proximal end section to the distal end section; a resonant frequency tracking section that automatically adjusts a frequency of the drive signal so as to track a resonant frequency of the ultrasound transducer and causes the distal end section to ultrasound-oscillate at the resonant frequency; a detecting section that detects from the drive signal a frequency component signal having a frequency component excluding the resonant frequency; and an output control section that performs control so as to vary an output of the drive signal that drives the ultrasound transducer, in accordance with a detection result of the detecting section.

A cavitation control method according to one aspect of the present invention includes: a step for applying ultrasound oscillation to a treatment object portion using an ultrasound transducer capable of generating ultrasound oscillation, a driving section that drives the ultrasound transducer by a drive signal, and a probe having a proximal end section operatively coupled to the ultrasound transducer and a distal end section that generates ultrasound oscillation for treating a tissue, the probe transmitting the ultrasound oscillation generated by the ultrasound transducer from the proximal end section to the distal end section; a detecting step for detecting a physical quantity that varies due to cavitation generated by ultrasound oscillation of the distal end section of the probe from the drive signal; and an output control step for controlling an output of the driving section so as to vary an oscillation of the distal end section in accordance with the physical quantity detected in the detecting step.

An ultrasound transducer control method according to one aspect of the present invention includes: a step for applying ultrasound oscillation to a treatment object portion using an ultrasound transducer capable of generating ultrasound oscillation, a driving section that drives the ultrasound transducer, and a probe having a proximal end section operatively coupled to the ultrasound transducer and a distal end section that generates ultrasound oscillation for treating a living tissue, the probe transmitting the ultrasound oscillation generated by the ultrasound transducer from the proximal end section to the distal end section; a resonant frequency tracking step for automatically adjusting a frequency of the drive signal so as to track a resonant frequency of the ultrasound transducer; a detecting step for detecting from the drive signal a frequency component excluding the resonant frequency; and an output control step for controlling an output of the driving section so as to vary the ultrasound oscillation of the distal end section in accordance with a detection result in the detecting step.

BRIEF DESCRIPTION OF THE DRAWINGS

FIG. 4A is a diagram showing a frequency distribution of a current signal detected from a drive signal during cavitation generation and cavitation non-generation;

FIGS. 4B to 4D are diagrams showing examples of characteristics indicating a frequency band transmitted by a filter circuit;

DETAILED DESCRIPTION OF PREFERRED EMBODIMENTS

Hereinafter, embodiments of the present invention will be described with reference to the drawings.

(First Embodiment)

Figure 1:
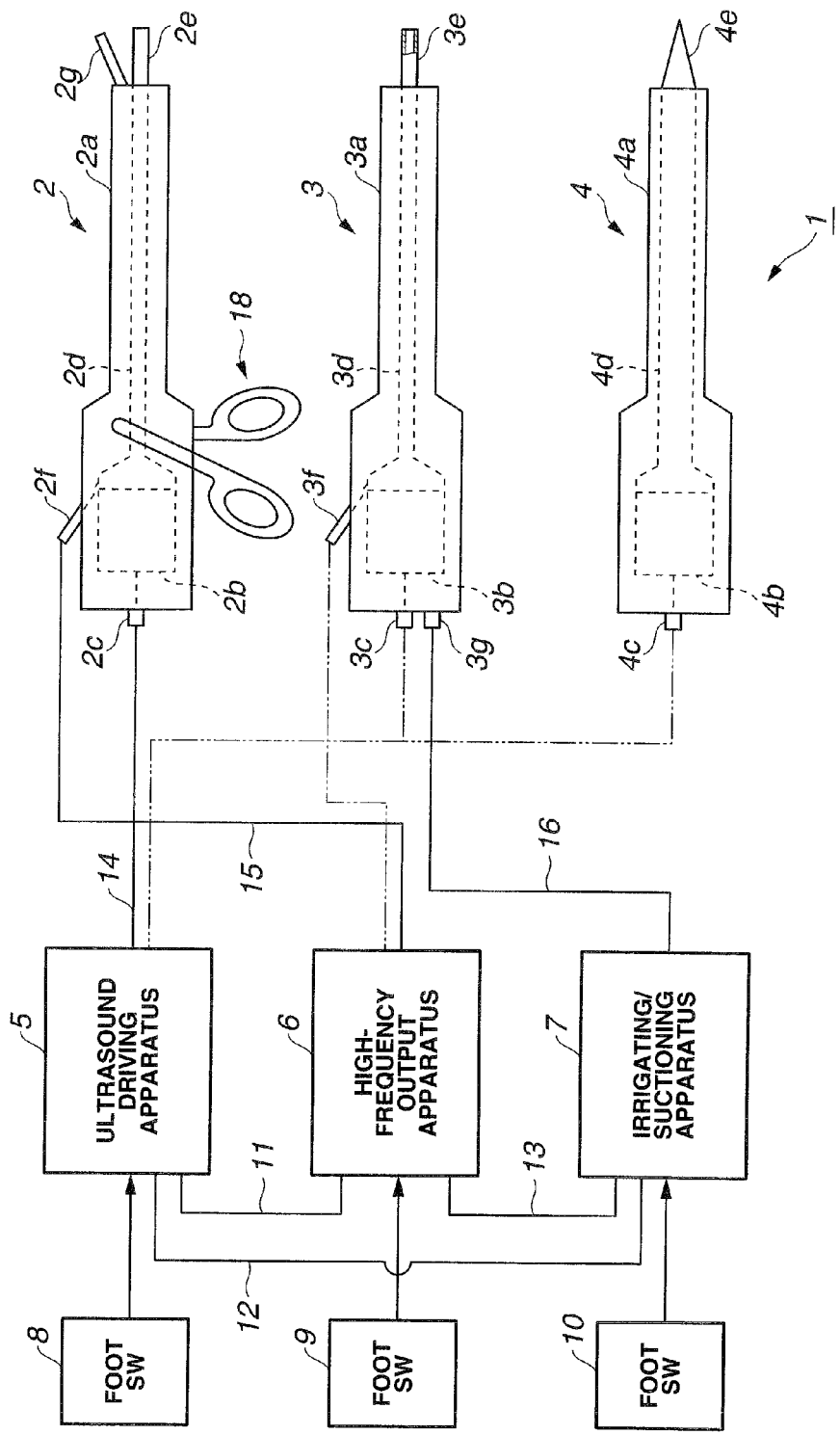
FIG. 1 is a configuration diagram showing a configuration of an ultrasound operation system including a first embodiment of the present invention.
Figure 2:
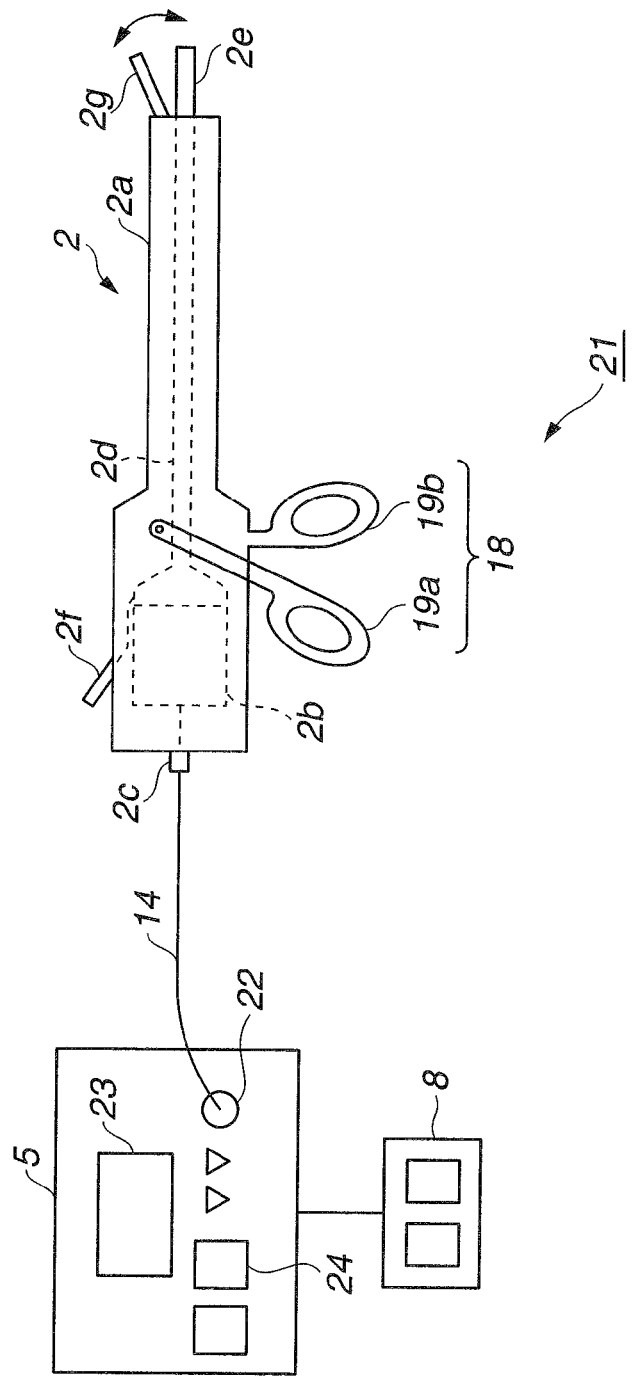
FIG. 2 is a configuration diagram of an ultrasound operation apparatus according to the first embodiment.
Figure 3:
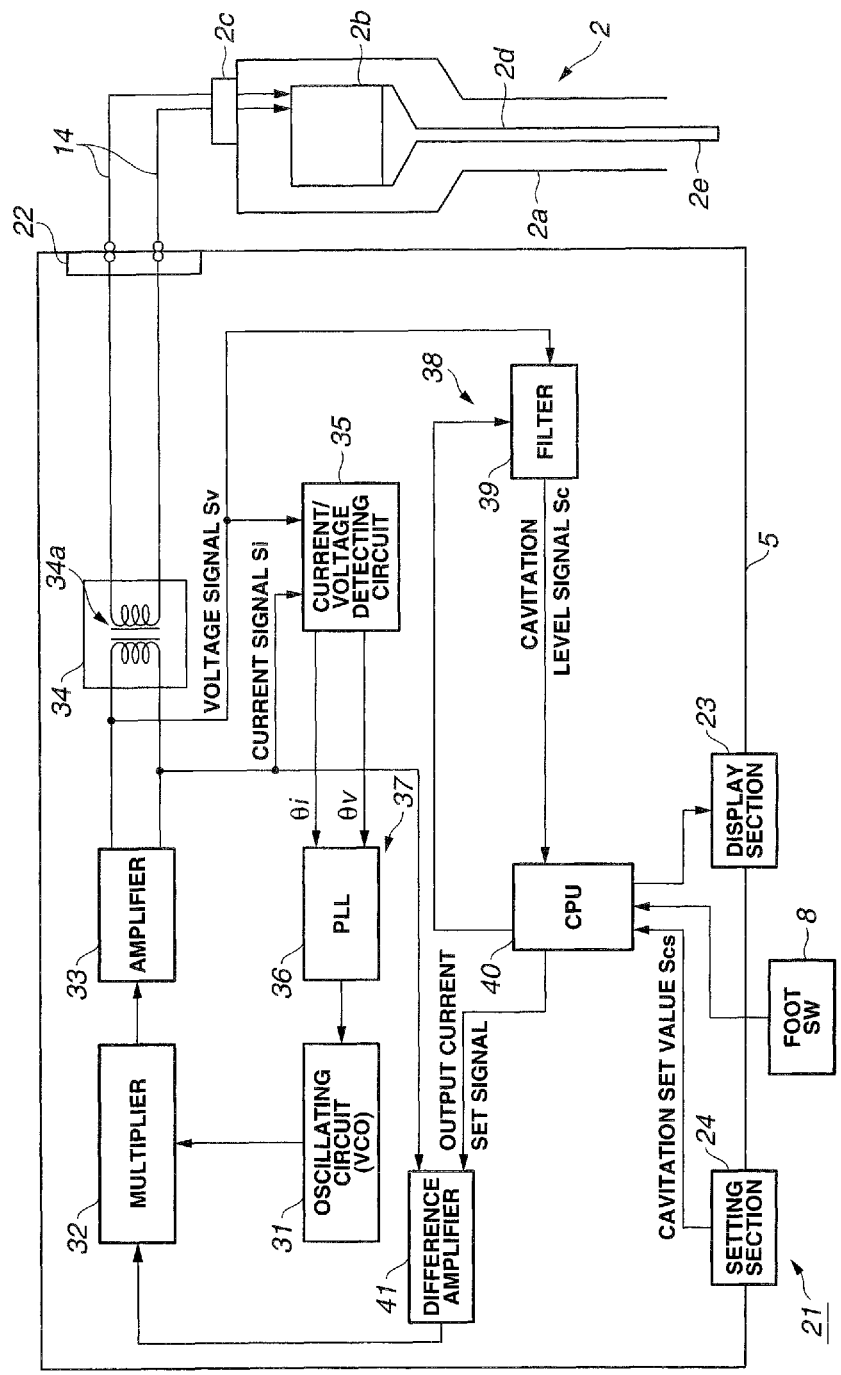
FIG. 3 is a block diagram showing a configuration of an ultrasound driving apparatus in an ultrasound operation apparatus.

FIGS. 1 to 9 are related to a first embodiment of the present invention, in which: FIG. 1 shows a configuration of an ultrasound operation system including the first embodiment of the present invention; FIG. 2 shows a configuration of an ultrasound operation apparatus according to the first embodiment; FIG. 3 shows a configuration of an ultrasound driving apparatus; and FIG. 4A shows a frequency distribution of a current signal detected from a drive signal during cavitation generation and cavitation non-generation. While a frequency distribution of a current signal is shown here, the same tendency will be exhibited by a voltage signal.

Figure 5:
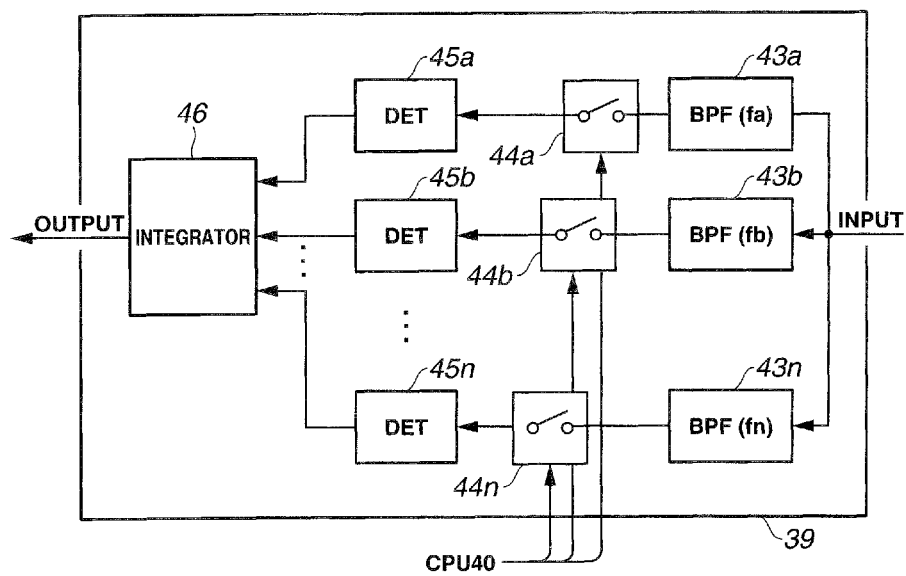
FIG. 5 is a block diagram showing a configuration example of a filter circuit.
Figure 6:
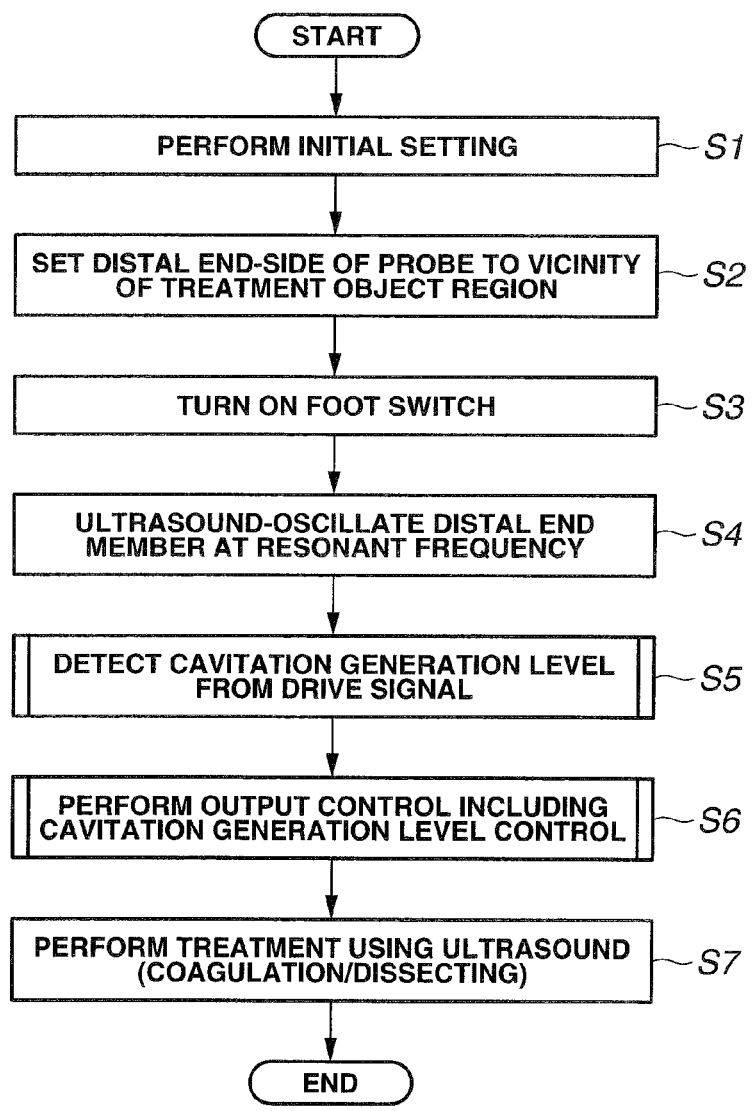
FIG. 6 is a flowchart showing a control method by an ultrasound operation apparatus.
Figure 7:
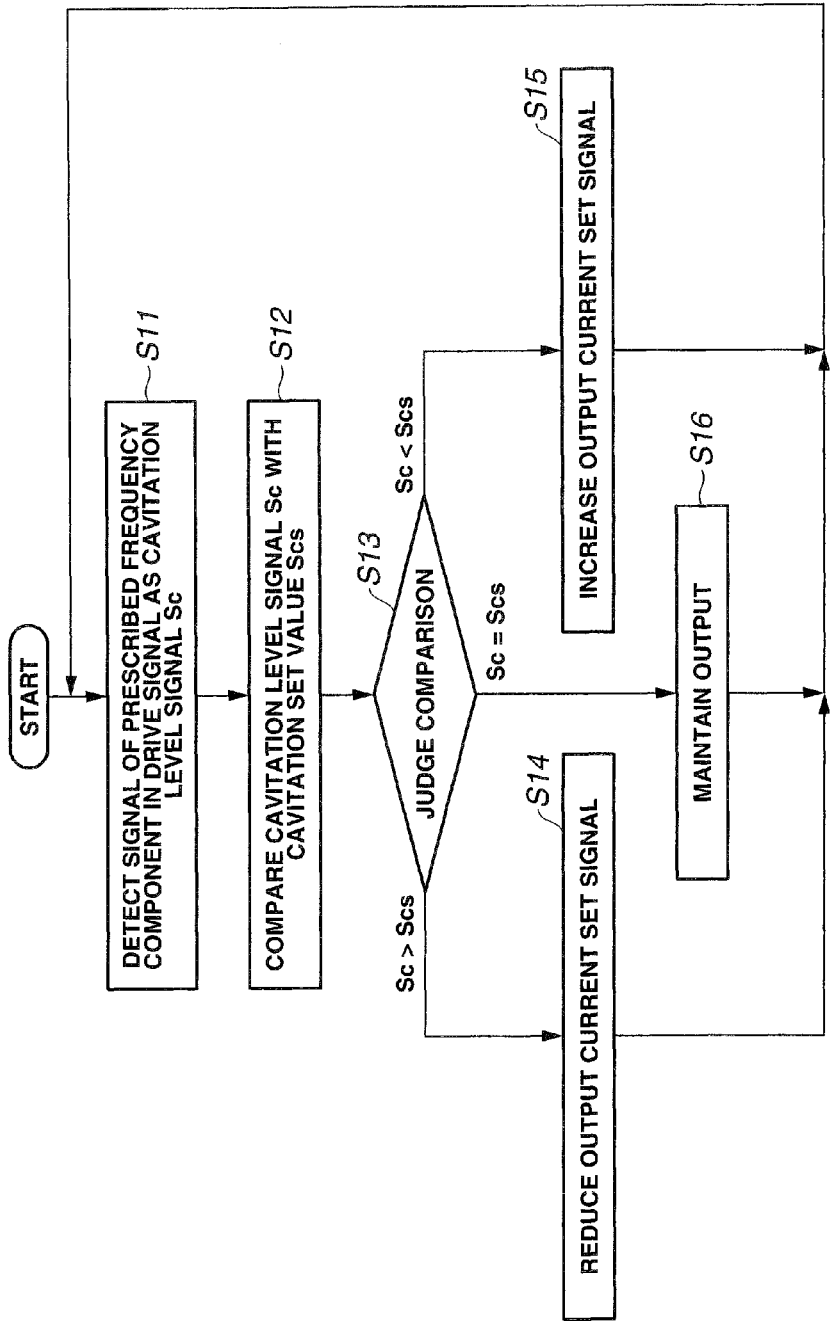
FIG. 7 is a flowchart showing a control method of a cavitation generation level as shown in FIG. 6.
Figure 8:
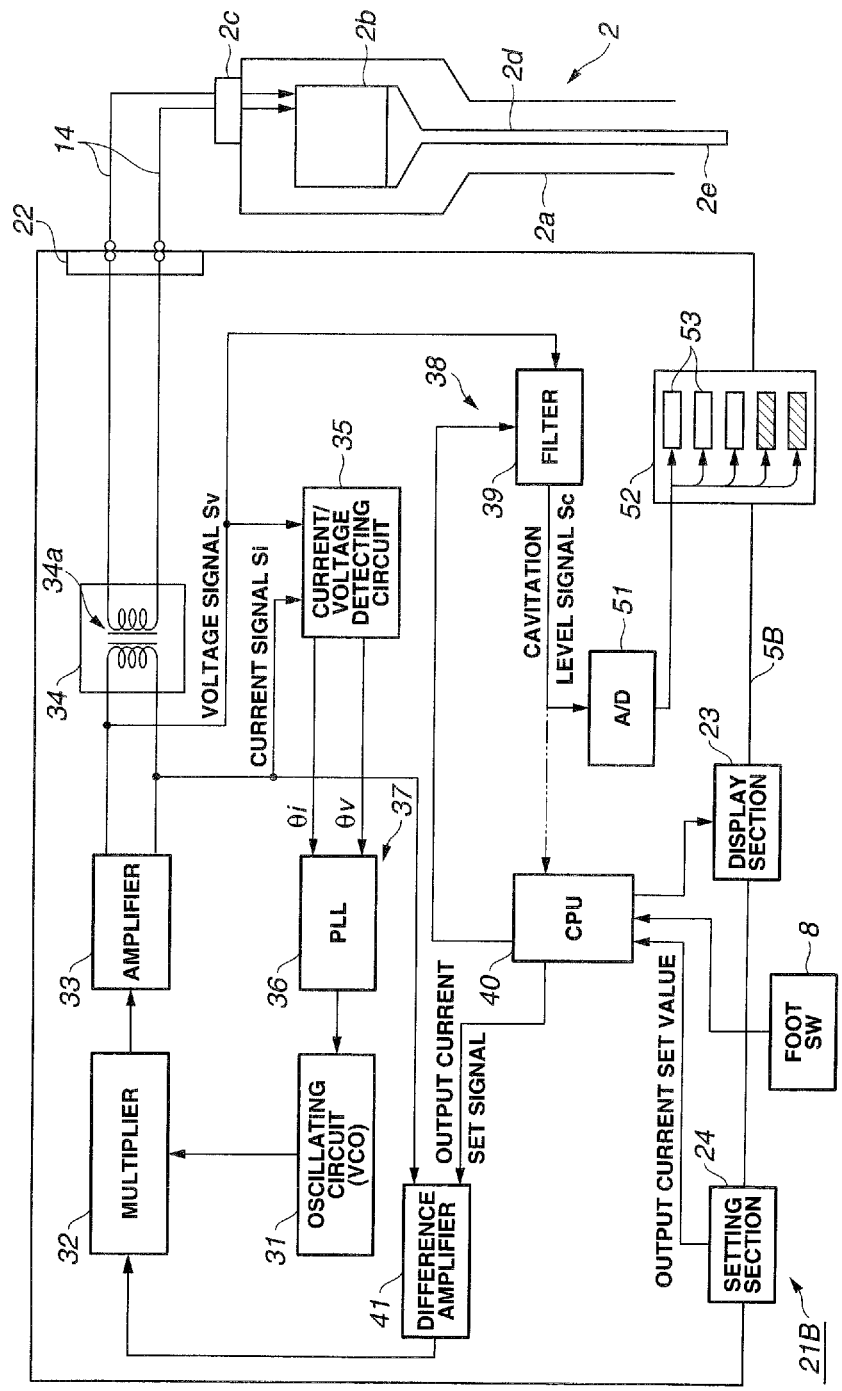
FIG. 8 is a block diagram showing a configuration of an ultrasound driving apparatus in an ultrasound operation apparatus according to a modification.
Figure 9:
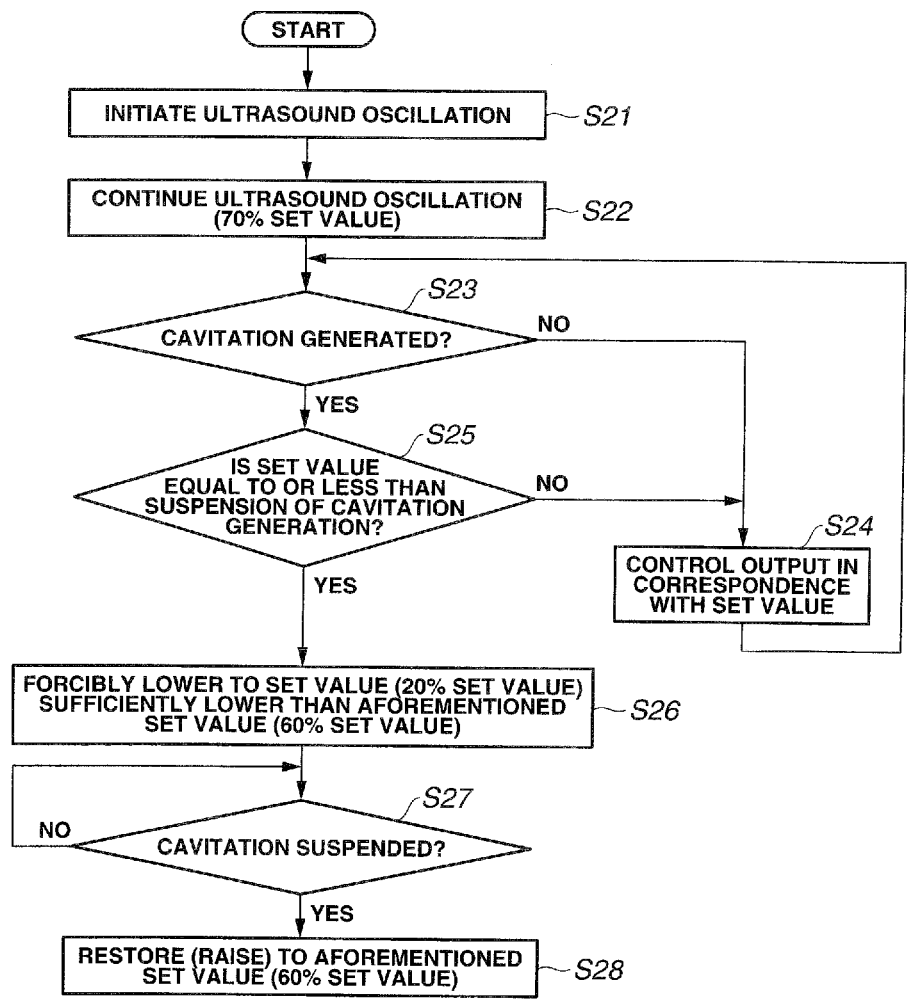
FIG. 9 is a flowchart showing a control method for reducing ultrasound output from the time of cavitation generation according to a modification.

FIGS. 4B to 4D show examples of filter characteristics of a filter circuit; FIG. 5 shows a configuration example of a filter circuit; FIG. 6 shows a control method by an ultrasound operation apparatus; FIG. 7 shows a control method for controlling a cavitation generation level as shown in FIG. 6; FIG. 8 shows a configuration of an ultrasound driving apparatus in an ultrasound operation apparatus according to a modification; and FIG. 9 shows an example of a control method for suspending cavitation generation from a state of cavitation generation according to a modification.

As shown in FIG. 1, an ultrasound operation system 1 according to the first embodiment of the present invention includes: a first handpiece 2 as an ultrasound coagulating/dissecting instrument that performs treatment such as coagulation, dissection, and exfoliation using ultrasound; a second handpiece 3 as an ultrasound suctioning instrument that performs treatment such as dissection, exfoliation, and fragmentation as well as suctioning using ultrasound; and a third handpiece 4 as an ultrasound puncturing instrument that performs treatment such as puncturing using ultrasound.

In addition, the ultrasound operation system 1 includes: an ultrasound driving apparatus 5 having a driving section that applies (outputs) an ultrasound drive signal to any actually connected handpiece among the first to third handpieces; a high-frequency output apparatus 6 that applies a high-frequency output signal to the actually connected handpiece of the first handpiece 2 and the second handpiece 3; and an irrigating/suctioning apparatus 7 that performs irrigation and suction in the case of the second handpiece 3 is connected.

Furthermore, foot switches 8, 9, and 10 are connected to the ultrasound driving apparatus 5, the high-frequency output apparatus 6, and the irrigating/suctioning apparatus 7, which respectively turn on/off output of the apparatuses 5, 6, and 7.

Moreover, the ultrasound driving apparatus 5 and the high-frequency output apparatus 6 are connected by a communication cable 11 that performs communication, the ultrasound driving apparatus 5 and the irrigating/suctioning apparatus 7 by a communication cable 12, and the high-frequency output apparatus 6 and the irrigating/suctioning apparatus 7 by a communication cable 13.

The respective handpieces I (I=2, 3, 4) among the first handpiece 2 to the third handpiece 4 have elongated probes 2a, 3a, 4a, and an ultrasound transducer (hereinafter simply transducer) Ib capable of generating ultrasound oscillation is built into a grasping section at which a proximal end section of each probe Ia is disposed. An ultrasound oscillation generated by the transducer Ib is operatively coupled at the proximal end section of a probe Ia to a horn which has, for example, an expanding diameter (in other words, coupled so that the ultrasound oscillation is transmittable to the proximal end section).

An ultrasound connector Ic electrically connected to the transducer Ib is provided at the proximal end of each handpiece I. The ultrasound connector Ic is connected to the ultrasound driving apparatus 5 via an attachable/detachable ultrasound cable 14.

When an operator turns on the foot switch 8, the ultrasound driving apparatus 5 outputs an ultrasound drive signal (hereinafter abbreviated as a drive signal) to the transducer Ib via the ultrasound cable 14. The transducer Ib ultrasound-oscillates when the drive signal is applied thereto.

The transducer Ib transmits the ultrasound oscillation to a distal end member Ie as a distal end section of the probe Ia via an ultrasound transmitting member Id inside the probe Ia, whereby the distal end member Ie ultrasound-oscillates.

The operator is capable of performing treatment using ultrasound oscillation by grasping the grasping section on the proximal end-side of the handpiece I and bringing the ultrasound-oscillating distal end member Ie into contact with living tissue that is a treatment object.

A high-frequency connector 2f provided on the proximal end-side of the handpiece 2 or a high-frequency connector 3f of the handpiece 3 is connected to the high-frequency output apparatus 6 via an attachable/detachable high-frequency cable 15. When the operator turns on the foot switch 9, the high-frequency output apparatus 6 outputs a high-frequency output signal to a conducting section inside the handpiece via the high-frequency cable 15. The conducting section is formed by the ultrasound transmitting member Id and, in a manner similar to the case of ultrasound oscillation, a high-frequency output signal is transmitted to the distal end member Ie at the distal end section of the probe Ia.

When the operator brings the distal end member Ie into contact with living tissue, a current of the high-frequency output signal (a high-frequency current) flows to the living tissue side. The operator uses the high-frequency current to perform high-frequency cauterization treatment on a living tissue portion that is in contact with the distal end member.

In this case, a return electrode (not shown) is disposed so as to come into contact with a patient over a wide area, whereby the high-frequency current flowing through the living tissue is returned through the return electrode to the high-frequency output apparatus 6 via a return cable connected to the return electrode.

In addition, in the handpiece 3, an ultrasound transmitting member 3d is formed as a conduit, wherein a hollow section of the conduit becomes a suction passage (irrigation is performed between the conduit of the transmitting member 3d and an outer sheath (not shown)). A distal end member 3e that is a distal end of the conduit is open.

An irrigation/suction connector 3g is provided on the proximal end-side of the handpiece 3. An irrigation/suction tube 16 attachably/detachably connected to the handpiece 3 is connected to the irrigating/suctioning apparatus 7.

For instance, inside the irrigating/suctioning apparatus 7, the irrigation/suction tube 16 branches to an irrigation conduit and a suction conduit, and the irrigation conduit is connected to an irrigating apparatus and the suction conduit to an suctioning apparatus.

When the operator performs an operation of the foot switch 10 to turn on an irrigation switch, an irrigating pump constituting the irrigating apparatus is activated and irrigation is performed. Irrigated water passes through the hollow section forming the ultrasound transmitting member 3d and is ejected from an opening of the distal end member 3e.

In addition, when the operator performs an operation of the foot switch 10 to turn on a suction switch, a suctioning pump constituting the suctioning apparatus is activated and a suction operation is performed. Accordingly, a piece of tissue or the like resulting from a treatment (fragmentation using ultrasound oscillation) is suctioned from the opening of the distal end member 3e and discharged to the suctioning apparatus.

While FIG. 1 shows a configuration example of a case where treatment is performed using, in combination, functions other than ultrasound oscillation, as shown in FIG. 2, an ultrasound operation apparatus 21 that performs treatment using only ultrasound oscillation may also be configured.

The ultrasound operation apparatus 21 shown in FIG. 2 includes, for example: a handpiece 2 that performs coagulation and dissection treatment by ultrasound oscillation; an ultrasound driving apparatus 5 that outputs a drive signal to the handpiece 2; and a foot switch 8 connected to the ultrasound driving apparatus 5, which turns on/off the output of the drive signal. The handpiece 2 is connected to a connector 22 of the ultrasound driving apparatus 5 via an ultrasound cable 14.

A handpiece 3 or a handpiece 4 may be connected to the ultrasound driving apparatus 5 in place of the handpiece 2. Moreover, as will be described in subsequent embodiments, treatment may be performed using, in combination, the high-frequency output apparatus 6.

As shown in FIG. 2, the handpiece 2 includes on a proximal end-side thereof a handle 18 to be grasped by the operator to perform opening/closing operations.

The handle 18 is supported at an upper end-side of a movable handle 19a by a pivoted section so as to be rotationally movable.

By performing opening/closing operations in which the movable handle 19a is closed to the side of a fixed handle 19b or opened to a separating side from the fixed handle 19b, a movable distal end member 2g adjacent to a distal end member 2e and supported so as to be rotationally movable can be open/closed with respect to the distal end member 2e via a wire, not shown, inserted through a probe 2a.

As described above, the handpiece 2 can be closed so as to grasp living tissue with the distal end member 2e as a fixed distal end member and the movable distal end member 2g, or be opened.

In other words, by applying ultrasound oscillation to living tissue with the living tissue grasped with the distal end members 2e and 2g, the handpiece 2 can generate frictional heat on the living tissue and perform coagulation and dissection treatment on the grasped living tissue. In addition, by setting the handpiece 2 to an open state in which a distal end-side is open, treatment such as fragmentation can be performed using the protruding distal end member 2e.

When performing treatment with the living tissue grasped, an operator normally desires to perform treatment while suppressing cavitation generation.

A front panel of the ultrasound driving apparatus 5 is provided with a display section 23 for displaying and a setting section 24 for setting a set value to be outputted as an ultrasound drive signal and the like.

FIG. 3 shows a configuration of the ultrasound driving apparatus 5 that constitutes the ultrasound operation apparatus 21 according to the present embodiment. Moreover, FIG. 3 shows a basic configuration portion of the handpiece 2 (the handpieces 3 and 4 are configured approximately the same) connected to the ultrasound driving apparatus 5. Hereinafter, while a case of I=2 as the handpiece I will be described, the description is applicable to I=3, 4 with the exception of structures unique to the handpiece 2.

The ultrasound driving apparatus 5 includes: an oscillating circuit 31; a multiplier 32 which receives an oscillation signal generated by the oscillating circuit 31 from one of input terminals thereof; an amplifier 33 that amplifies a signal multiplied by the multiplier 32; and an output circuit 34 that insulates and outputs a drive signal amplified by the amplifier 33.

The output circuit 34 is constituted by, for example, a transformer 34a. A drive signal amplified by the amplifier 33 is inputted to a primary winding of the transformer 34a, and a drive signal insulated from a primary winding-side drive signal is outputted from a secondary winding electromagnetically coupled to the primary winding. Moreover, the primary winding-side of the transformer 34a forms a secondary circuit while the secondary winding-side forms a patient circuit.

A patient circuit-side output terminal connector 22 from which a drive signal is to be outputted is connected via an attachably/detachably connected ultrasound cable 14 to a transducer 2b built into the handpiece 2 that ultrasound-oscillates is connected.

In addition, the primary winding of the transformer 34a is connected to a current/voltage detecting circuit 35 that detects a drive signal current flowing through the primary winding and a voltage between both ends of the primary winding and, at the same time, detects a current phase and a voltage phase.

A current phase signal θi and a voltage phase signal θv detected by the current/voltage detecting circuit 35 are outputted to a PLL (phase lock loop) circuit 36.

The PLL circuit 36 applies a control signal whose output signal level varies in accordance with a phase difference between an inputted current phase signal θi and a voltage phase signal θv to the oscillating circuit 31. An oscillating frequency of the oscillating circuit 31 varies according to a signal level applied to a control input terminal. In other words, the oscillating circuit 31 is formed by, for example, a voltage control oscillating circuit (VCO).

The PLL circuit 36 applies a control signal for controlling to reduce the phase difference between the current phase signal θi and the voltage phase signal θv or, in other words, an oscillating frequency adjustment signal as described below to the control input terminal of the oscillating circuit 31. Therefore, by a closed loop using the PLL circuit 36, the oscillating frequency of the oscillating circuit 31 is automatically adjusted so that the phase difference between the current phase signal θi and the voltage phase signal θv equals 0.

A state in which the phase difference between the current phase signal θi and the voltage phase signal θv equals 0 becomes a drive frequency corresponding to a resonant frequency of the transducer 2b. Therefore, the PLL circuit 36 automatically adjusts (controls) the oscillating frequency so as to drive the transducer 2b according to a drive signal of the resonant frequency of the transducer 2b.

In other words, when the transducer 2b is driven with a drive signal, a closed-loop circuit system made up of the oscillating circuit 31 to the PLL circuit 36 forms a resonant frequency tracking section 37 that automatically adjusts the drive signal frequency so as to track the resonant frequency of the transducer 2b. The resonant frequency tracking section 37 constitutes a driving section that outputs a resonant frequency drive signal.

Furthermore, as described below, the present embodiment is provided with a detecting section 38 that detects cavitation generated at the distal end member 2e of the probe 2a (to which the ultrasound oscillation of the transducer 2b has been transmitted) as a physical quantity that varies due to the cavitation from a drive signal of the primary winding side of the output circuit 34 described above.

For example, a voltage signal Sv as a physical quantity of the drive signal which varies due to the cavitation is inputted to a filter circuit 39 having a frequency transmission characteristic (filtering characteristic) for extracting a prescribed frequency component. Moreover, as will be described later, a current of the drive signal is controlled so as to become a constant current at a prescribed time constant. Therefore, a detection (through the filter circuit 39) of a voltage value of the voltage signal Sv becomes approximately equivalent to a detection of an impedance value.

Moreover, in addition to detecting a voltage value or an impedance value as the aforementioned physical quantity, for example, the detecting section 38 may detect a current value of a current signal in a state where the voltage signal Sv is controlled so as to become a constant voltage at a prescribed time constant.

The filter circuit 39 has a characteristic of transmitting at least a prescribed frequency component other than the resonant frequency (i.e., drive frequency) of the transducer 2b driven by the drive signal.

A voltage signal as a frequency component signal of a prescribed frequency component outputted from the filter circuit 39 becomes a signal corresponding to a generation level of cavitation generated by the transducer 2b or, in other words, a cavitation level signal Sc.

The aforementioned detecting section 38 is constituted using the filter circuit 39 that generates the cavitation level signal Sc. Moreover, the detecting section 38 may be regarded as a configuration including a CPU 40 that judges the presence/absence of cavitation and a generation level of the cavitation from the cavitation level signal Sc.

The cavitation level signal Sc outputted from the filter circuit 39 is inputted to the central processing unit (CPU) 40 as a control section that controls the respective sections of the ultrasound driving apparatus 5.

In addition, the CPU 40 also has the function of an output control section that variably controls an output value of a drive signal that determines an amplitude of an ultrasound oscillation of the distal end member 2e of the probe 2a from a physical quantity detected by the detecting section 38. In other words, the CPU 40 has the function of a control section that changes and controls a drive signal that drives the transducer 2b.

The CPU 40 judges a cavitation generation level from the level of an inputted cavitation level signal Sc.

FIG. 4A shows frequency spectrum distributions of a voltage signal Sv when cavitation is not generated (during non-generation of cavitation) by a transducer 2b driven by a drive signal of the ultrasound driving apparatus 5 and when cavitation is generated (during cavitation generation). In FIG. 4A, it is assumed that a resonant frequency fres is 47 kHz.

Regardless of whether cavitation is generated or not, at the resonant frequency fres (47 kHz), the voltage signal Sv has a highest peak. During cavitation non-generation, the voltage signal Sv does not have a significant peak in frequencies other than the resonant frequency fres.

In contrast, during cavitation generation, the level of the voltage signal Sv in frequencies other than the resonant frequency fres are higher than during cavitation non-generation.

Specifically, during cavitation generation, levels in subharmonics of the resonant frequency fres such as frequencies of divisors including ½, ¼, and the like or differences of the divisors are significantly higher than during cavitation non-generation and, at the same time, levels of frequency components other than subharmonics are also higher than during cavitation non-generation.

Therefore, as described above, by detecting a signal level of the voltage signal Sv excluding the vicinity of the resonant frequency fres, a cavitation generation level can be detected.

The cavitation level signal Sc as an output signal of the filter circuit 39 is inputted to the CPU 40 constituting an output control section that controls driving of the transducer 2b (in other words, the ultrasound oscillation of the distal end member 2e).

In response to the cavitation level signal Sc inputted from the filter circuit 39, the CPU 40 outputs an output current set signal corresponding to a difference value from a cavitation level set value Scs set by an operator through the setting section 24 to a difference amplifier 41.

A current signal Si of the drive signal is also inputted to the difference amplifier 41. While the current signal Si is detected by, for example, a current sensor or the like which is provided in the current/voltage detecting circuit 35 and detects a current of the drive signal, FIG. 3 simplistically shows a detected current signal Si.

The difference amplifier 41 outputs to the multiplier 32 a signal of a difference value obtained by subtracting the current signal Si from the output current set signal.

The multiplier 32 multiplies a value of the other input terminal-side to which a signal from the difference amplifier 41 is inputted, by an oscillation signal from the oscillating circuit 31, and outputs the product to the amplifier 33. In this case, the value of the other input terminal-side is a sum obtained by adding an output signal of the difference amplifier 41 to a reference value 1 (subtracted therefrom when the output signal of the difference amplifier 41 is negative).

Therefore, the current signal Si of the drive signal is controlled by the closed-loop system to maintain as a constant current value having, as an average, a value of an output current set signal outputted from the CPU 40. In this manner, the output value of the drive signal supplied to the transducer 2b is controlled.

A time constant of a control system based on the current signal Si of the drive signal is, for example, around 8 ms. The current signal Si varies within a range of the time constant.

An operation signal that turns on/off an output of the drive signal from the foot switch 8 is inputted to the CPU 40.

In addition, the CPU 40 is connected to the display section 23 provided on a front panel or the like. An ultrasound output value or the like is displayed on the display section 23. FIGS. 4B and 4C show examples of filter characteristics of the filter circuit 39, and FIG. 5 shows a configuration example of the filter circuit 39.

FIG. 4B shows a case in which a characteristic is set to transmit a portion of frequency bands on, a low frequency-side, for example. More specifically, a characteristic is set to transmit a frequency band including frequencies a subharmonic (divisor), ½ of the resonant frequency fres.

FIG. 4C shows a case in which a band characteristic is set to transmit frequencies from around 5% of the resonant frequency fres to 5% lower than the resonant frequency fres (i.e., a frequency of 95% of the resonant frequency fres).

FIG. 4D shows the band characteristic of FIG. 4C, as well as a case in which a band characteristic is set to transmit frequencies from 5% higher than the resonant frequency fres to 5% lower than a frequency (2fres) of a secondary harmonic of the resonant frequency fres.

The filter circuit 39 shown in FIG. 5 is constituted by, for example, a plurality of bandpass filters (hereinafter abbreviated as BPFs in FIG. 5) 43a, 43b, ..., 43n, a plurality of switches 44a, 44b, ..., 44n, a plurality of wave detectors 45a, 45b, 45n, and an integrator 46.

Passing frequency bands of the bandpass filters 43a, 43b, ..., 43n are simplistically shown as fa, fb, ..., fn. In this case, for example, the passing frequency bands have a relationship expressed as fa<fb<...<fn.

The on/off of the switches 44a, 44b, ..., 44n can be selected via the CPU 40 by, for example, a setting made through the setting section 24. In this case, a selection may be made directly from the setting section 24.

An arbitrary passing frequency band can be set by selecting the on/off of the switches 44a, 44b, 44n. A frequency component having passed through the switches 44a, 44b, 44n which have been turned on is first detected by the wave detectors 45a, 45b, 45n and then integrated by the integrator 46.

An integral signal integrated by the integrator 46 is outputted to the CPU 40 as a cavitation level signal Sc. An accumulator may be used in place of the integrator 46.

Moreover, instead of integrating at the filter circuit 39, integration may be performed on the CPU 40 side.

Operations of the ultrasound driving apparatus 5 configured as presented above will now be described with reference to FIG. 6. FIG. 6 shows an ultrasound operation control method including cavitation control performed by the ultrasound driving apparatus 5.

For example, as shown in FIG. 2, an operator connects a handpiece to be used for treatment (in FIG. 2, the handpiece 2 primarily used to perform coagulating/dissecting) to the ultrasound driving apparatus 5 via an ultrasound cable.

In addition, in accordance with living tissue to be treated (i.e., a region to be treated), as shown in step S1, the operator performs initial setting including setting a cavitation level set value Scs with the setting section 24.

Next, by using a trocar, not shown, an endoscope and the probe 2a of the handpiece 2 are pierced into the abdomen or the like of a patient. Then, as shown in step S2, under observation through the endoscope, the operator sets a distal end-side of the probe 2a inside the body to the vicinity of a treatment object region.

In a next step S3, the operator turns on the foot switch 8 and commences ultrasound treatment. A drive signal is applied to the transducer 2b of the handpiece 2 from the ultrasound driving apparatus 5, causing the transducer 2b to ultrasound-oscillate.

The ultrasound oscillation is transmitted to the distal end member 2e on the distal end-side of the probe 2a. As shown in step S4, the distal end member 2e ultrasound-oscillates at the resonant frequency fres of the transducer 2b.

In this case, with the resonant frequency tracking section 37 using the PLL circuit 36, the ultrasound driving apparatus 5 controls the transducer 2b so as to track a state where the transducer 2b is driven at the resonant frequency fres. Therefore, the transducer 2b ultrasound-oscillates at the resonant frequency fres and the distal end member 2e of the distal end section also ultrasound-oscillates at the resonant frequency fres.

Furthermore, in this case, when cavitation occurs due to the ultrasound oscillation of the distal end member 2e, the distal end member 2e is subjected to a destruction force of small bubbles due to the generation of the cavitation, and the force affects an ultrasound oscillation of the transducer 2b, from the distal end member 2e. In addition, as shown in FIG. 4A, a frequency component due to cavitation is superposed on the original drive signal. As described above, due to the generation of the cavitation, a frequency spectrum of the original drive signal now includes a distorted frequency spectrum.

Then, as shown in FIG. 5, the CPU 40 detects a cavitation generation level from the cavitation level signal Sc detected by the filter circuit 39 from the drive signal.

In the following step S6, the CPU 40 controls the output of the drive signal via the difference amplifier 41 so that the detected cavitation generation level becomes the cavitation level set value Scs set in advance by the setting section 24. In other words, the CPU 40 controls the cavitation generation level to perform output control of the drive signal.

Under such control, as shown in step S7, the operator performs treatment such as coagulating and dissecting using ultrasound oscillation.

FIG. 7 shows operations for detecting a cavitation level in steps S5 and S6 in FIG. 6, and controlling a generation level of the cavitation, that is, the cavitation level according to a detection result. In step S11, the filter circuit 39 detects, as a cavitation level signal Sc, a prescribed frequency component excluding the frequency of the drive signal.

In the following step S12, the CPU 40 compares the cavitation level signal Sc outputted from the filter circuit 39 with the cavitation level set value Scs.

Then, as shown in step S13, the CPU 40 judges a magnitude relation between the two. When the comparison result is Sc>Scs, as shown in step S14, the CPU 40 performs control so as to reduce an output current set signal and returns to the processing in step S11.

When the comparison result is the opposite, in other words, Sc<Scs, as shown in step S15, the CPU 40 performs control so as to increase the output current set signal and returns to the processing in step S11.

In addition, when the comparison result is Sc=Scs, as shown in step S16, the CPU 40 performs control so as not to change the output current set signal (maintain the output current). In this control state, as shown in FIG. 6, the operator performs treatment using ultrasound oscillation in step S7.

By performing such control, the CPU 40 that configures an output control section controls the cavitation generation level so as to maintain the set value set by the setting section 24.

According to the present embodiment in which treatment is performed under such control on the living tissue as a treatment object, it is possible to detect the generation of cavitation and control the generation level of the cavitation so as to maintain a set cavitation level set value Scs with a simple configuration.

In this case, with a simple configuration, the generation of cavitation can be detected with high accuracy from a voltage signal or the like of a frequency component excluding a drive frequency based on the filter circuit 39 or the resonant frequency fres, of a drive signal that drives the transducer 2b.

In addition, according to the present embodiment, the function of therapeutic treatment can be improved by effectively using cavitation generation.

Furthermore, side-effects due to cavitation can be reduced by controlling the cavitation generation level.

Note that, Japanese Patent Application Laid-Open Publication No. 2008-188160 as an example of related art discloses a configuration of an ultrasound operation apparatus having a drive circuit that drives a handpiece at a frequency and an amplitude in accordance with alternating current, in which the ultrasound operation apparatus is provided with a cavitation suppressing circuit including: converting means for converting an output terminal voltage of the drive circuit into a direct current voltage; comparing means for comparing the direct current voltage obtained by the converting means with a predetermined threshold; and voltage control means that lowers an alternating current voltage value when a comparison result by the comparing means exceeds the threshold.

In the related-art example, it is described that the ultrasound operation apparatus is an application of the fact that when a load state of a piezoelement constituting an oscillation generating section varies due to the generation of cavitation, while an alternating current voltage value outputted by an output circuit (including a drive circuit) remains virtually unchanged, an output voltage value varies in proportion to the load state.

In contrast to the related-art example, in the present embodiment, cavitation is detected using a voltage value, an impedance value, and a current value of at least a frequency component of a drive signal excluding the vicinity of a frequency used for driving.

Therefore, the present embodiment is capable of sufficiently reducing the influence of a drive signal to detect, at high accuracy, the presence/absence of cavitation generation, and the generation level.

In other words, in the present embodiment, by detecting a frequency component excluding the vicinity of the frequency of the drive signal, a cavitation generation level can be detected from, for example, the level of the cavitation level signal Sc with little influence from the output level of the drive signal.

In this case, the presence/absence of cavitation generation can be judged depending on whether or not the level of the cavitation level signal Sc is equal to or greater than a threshold approximating 0. In addition, a cavitation generation level can be detected even when an operator varies a set value with the setting section 24 so as to vary the output level of a drive signal during an operation.

In contrast, the related-art example requires that a threshold be set in advance for detecting cavitation generation, and it is therefore conceivable that the threshold requires to be changed when the output of the drive circuit is varied.

Furthermore, the related-art example discloses a configuration further provided with a microphone that detects a continuous sound of a frequency generated during cavitation, in which cavitation control is performed using an audio signal outputted by the microphone.

However, in this case, it is necessary to provide the microphone on a distal end-side of an elongated probe 2a insertable into a body.

In contrast, according to the present embodiment, the presence/absence of cavitation generation and the generation level can be detected by the side of the ultrasound driving apparatus 5 placed outside of a body. In addition, as for the configuration of the probe itself, existing probes and handpieces can be employed.

Therefore, the present embodiment is advantageous in being readily applicable to an existing handpiece provided with a transducer.

Moreover, as a detecting section that detects cavitation, the presence/absence of cavitation generation may detected by detecting a signal of, for example, a subharmonic component excluding a resonant frequency fres or by amplifying and comparing the signal using a comparator.

In addition, when cavitation is detected, the presence/absence of cavitation generation may be detected from a temporal variation of a signal excluding the resonant frequency fres after the time of initiation of ultrasound oscillation which is assumed to be 0.

FIG. 8 shows a configuration of an ultrasound operation apparatus 21B according to a modification. In the first embodiment, the configuration has been described in which a cavitation generation level is automatically controlled so as to take a set value.

In contrast, the present modification is configured to include a notifying section that notifies a cavitation generation level to an operator as a user by way of quantitative display, whereby the operator is capable of manually changing a displayed level to set a set value of a setting section 24 to a desired cavitation level.

The ultrasound operation apparatus 21B is configured to replace the ultrasound driving apparatus 5 having the configuration shown in FIG. 3 with an ultrasound driving apparatus 5B which includes: an A/D converting circuit 51 for A/D-converting an output signal of the filter circuit 39; and an indicator 52 as a notifying section that quantitatively indicates a cavitation generation level from an output signal of the A/D converting circuit 51.

A cavitation level signal Sc outputted from the filter circuit 39 is A/D-converted by the A/D converting circuit 51. The A/D-converted digital signal corresponds to the cavitation generation level.

The digital signal causes, for example, a plurality of LEDs 53 constituting the indicator 52 to become luminous. For example, the number of luminous LEDs 53 varies almost proportionally to the cavitation generation level. In FIG. 8, for example, two LEDs 53 indicated by diagonal lines are luminous. As the cavitation generation level rises, more LEDs 53 become luminous.

In the present modification, an output current set value set by the operator from the setting section 24 is inputted to the CPU 40, whereby the CPU 40 outputs an output current set signal that maintains a difference value from the output current set value from the setting section 24 to the difference amplifier 41.

Moreover, in the case of the present modification, a drive signal to the transducer 2b (more generally, the transducer Ib) is subjected to output control by the CPU 40 so as to maintain the output current set value. Other configurations are the same as those in the first embodiment.

In the present modification, the operator can confirm the cavitation generation level through display by the number of luminous LEDs 53 of the indicator 52. Having confirmed the cavitation generation level, the operator can perform treatment at an output current set value that enables treatment to be readily performed by setting the output current set value lower than the cavitation generation level or setting a higher output current set value.

According to the present modification, the operator is capable of performing treatment at a set value desired by the operator with reference to the indicator 52 that notifies a cavitation generation level through display. Moreover, besides notification to the operator by a display apparatus, the notifying section may be configured to notify the operator through sound or the like.

In addition, the functions of the indicator 52 as a notifying section may instead be provided at the display section 23. For example, though the indicator 52 is not shown in embodiments and the like subsequent to FIG. 8, the functions of the indicator 52 may be performed by the display section 23.

Moreover, the modification shown in FIG. 8 may be configured so that the cavitation level signal Sc of the filter circuit 39 is also inputted to the CPU 40 as indicated by the dashed two-dotted line to monitor the presence/absence of cavitation generation and facilitate setting from a cavitation generated state to a cavitation non-generated state.

Cavitation exhibits a hysteresis characteristic, and exhibits in come cases a characteristic in which once cavitation is generated, cavitation does not stop even if a set level of a drive signal is lowered to an output level immediately preceding cavitation generation.

Consequently, by adopting a control method such as shown in FIG. 9, more preferable responsiveness can be secured and an output level at which cavitation is not generated can be set in a short period of time.

It is assumed that, in the first step S21, the transducer 2b and the distal end member 2e of the handpiece 2 initiate ultrasound oscillation, and in the next step S22, the ultrasound oscillation continues at 70% of a maximum set value (hereinafter abbreviated as 70% set value).

In this case, as shown in step S23, the CPU 40 judges the presence/absence of cavitation generation from the output signal of the filter circuit 39.

When it is judged in step S23 that cavitation is not generated, the routine proceeds to step S24 in which the CPU 40 performs output control corresponding to a set value set by the operator with the setting section 24. The routine then returns to step S23. In other words, when cavitation is not generated, the CPU 40 performs output control so as to maintain the set value corresponding to the set value manually set by the operator.

On the other hand, when it is judged that cavitation is generated, the routine proceeds to step S25. In step S25, the CPU 40 judges whether or not the operator has lowered the set value (without considering the hysteresis characteristic) to or below the set value at which cavitation generation is suspended.

When the operator varies the set value within a range in which cavitation generation is not suspended, the routine returns to step S23 via step S24.

In contrast, when the operator has lowered the set value to or below a set value at which cavitation generation is suspended (for example, 60% set value), as shown in step S26, the CPU 40 temporarily forcibly lowers the set value to a significantly low set value that is drastically lower than the set value at which cavitation generation is suspended (for example, lowered to 20% set value).

In other words, even when cavitation exhibits the hysteresis characteristic, the set value is forcibly (temporarily) lowered to a set value at which cavitation generation is promptly suspended.

In this state, as shown in step S27, the CPU 40 monitors the output signal of the filter circuit 39 and waits for cavitation generation to be suspended. After cavitation generation is suspended, as shown in step S28, the CPU 40 restores the set value from the forcibly lowered set value to the set value set by the operator (the aforementioned 60% set value).

By performing such control, when the operator changes the setting to a set value at which cavitation generation is suspended in a state of cavitation generation, ultrasound oscillation can be set to an output state of an original set value within a short period of time even when the hysteresis characteristic is exhibited.

Though in the embodiment described above, processing of step S26 is performed after the operator performs treatment in step S25, automatic control may be performed in which a transition to step S26 is automatically made upon detection of cavitation generation without any treatment performed in step S25.

Moreover, the CPU 40 may wait for a lapse of a certain amount of time instead of performing the judgment of step S27 shown in FIG. 9 in which the CPU 40 awaits cavitation suspension. The certain amount of time in this case is preferably set to, for example, a sum obtained by adding a margin to the time required for cavitation suspension.

The control method shown in FIG. 9 may be used in a case where cavitation generation is suspended (or eliminated) from a state of cavitation generation. In addition, the control method may be used in a case of suppressing the amount of generated cavitation within a short period of time.

(Second Embodiment)

Next, a second embodiment of the present invention will be described with reference to FIG. 10. The present embodiment enables the selection between two control modes or control patterns with different control contents, namely, a normal constant current (constant amplitude) control mode and a cavitation control mode, and enables treatment using ultrasound oscillation.

Moreover, in a modification of the present embodiment, control set to a control mode in accordance with a type or a use condition of a handpiece as a treatment instrument using ultrasound oscillation can also be performed.

Figure 10:
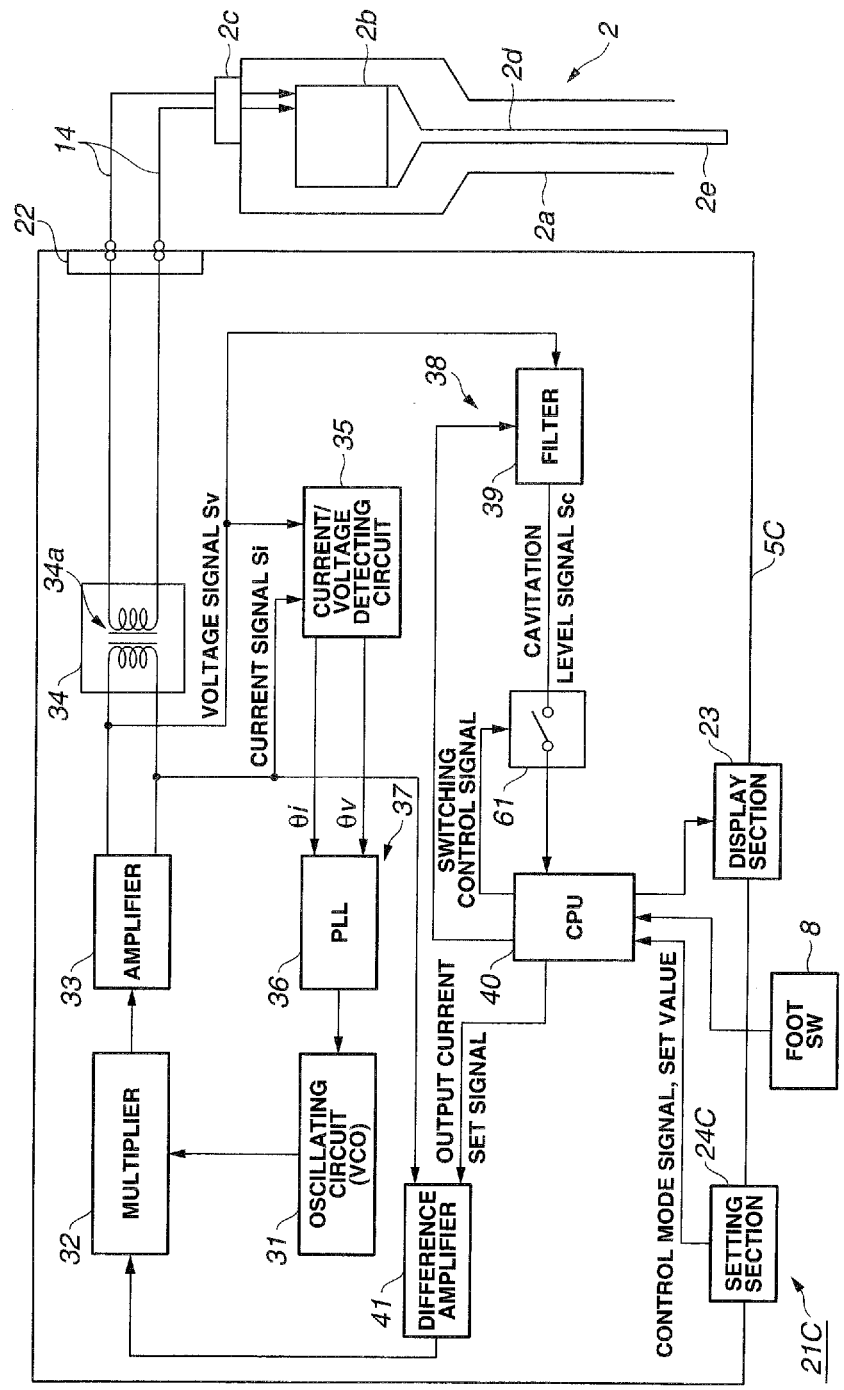
FIG. 10 is a configuration diagram of an ultrasound operation apparatus according to a second embodiment of the present invention.

An ultrasound operation apparatus 21C according to the second embodiment shown in FIG. 10 is provided with an ultrasound driving apparatus 5C that is configured by adding to the ultrasound driving apparatus 5 of the ultrasound operation apparatus 21 shown in FIG. 3 a relay apparatus 61 switched by a switching control signal provided between the filter circuit 39 and the CPU 40 constituting an output control section.

The relay apparatus 61 is switched between on/off by a switching control signal from the CPU 40 to the switch control modes. In other words, the output control section is further provided with a control switching section that switches the control modes.

Figure 11:
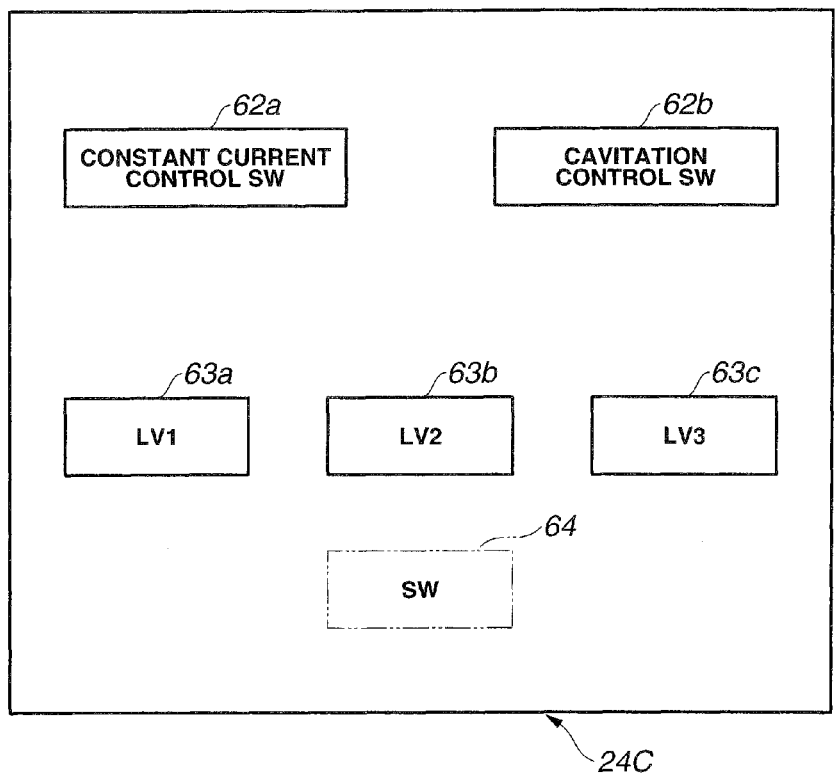
FIG. 11 is a diagram showing a setting section that selectively sets a plurality of control modes.

In addition, the ultrasound driving apparatus 5C according to the present embodiment includes, for example, a setting section 24C shown in FIG. 11.

The setting section 24C is provided with: a constant current control switch 62a by which an operator selectively instructs the constant current control mode; and a cavitation control switch 62b by which the operator selectively instructs the cavitation control mode.

Furthermore, the setting section 24C is provided with level switches 63a, 63b, and 63c that set output levels in both control modes to a plurality of stages. For example, the level switches 63a, 63b, and 63c set output levels to LV1, LV2, and LV3, respectively.

Consequently, the setting section 24C outputs to the CPU 40 a control mode signal that instructs either the constant current control mode or the cavitation control mode and a set value that sets the output level.

Moreover, though the level switches 63j (j=a to c) are shown in FIG. 11 as the switches having configurations to be commonly used in both control modes at the time of level setting, sets of level switches may be provided instead in which each set is dedicated to each control mode and made up of, for example, a plurality of level switches.

In the configuration shown in FIG. 10, the CPU 40 performs output control in accordance with a control mode set by the operator with the setting section 24C.

Specifically, when the constant current control mode is selected, the CPU 40 outputs a switching control signal that switches a switch of the relay apparatus 61 to off. The CPU 40 then outputs an output current set signal to the difference amplifier 41 so as to maintain output levels of the level switches 63j (j=a to c) of the setting section 24C.

In contrast, when the cavitation control mode is selected, the CPU 40 outputs a switching control signal that switches the switch of the relay apparatus 61 to on. Therefore, a cavitation level signal Sc from the filter circuit 39 is inputted to the CPU 40 via the relay apparatus 61 that has been turned on.

The CPU 40 then outputs the cavitation level signal Sc to the difference amplifier 41 as an output current set signal so as to maintain the output levels of the level switches 63j (j=a to c) of the setting section 24C set as the cavitation control mode by the operator.

Figure 12:
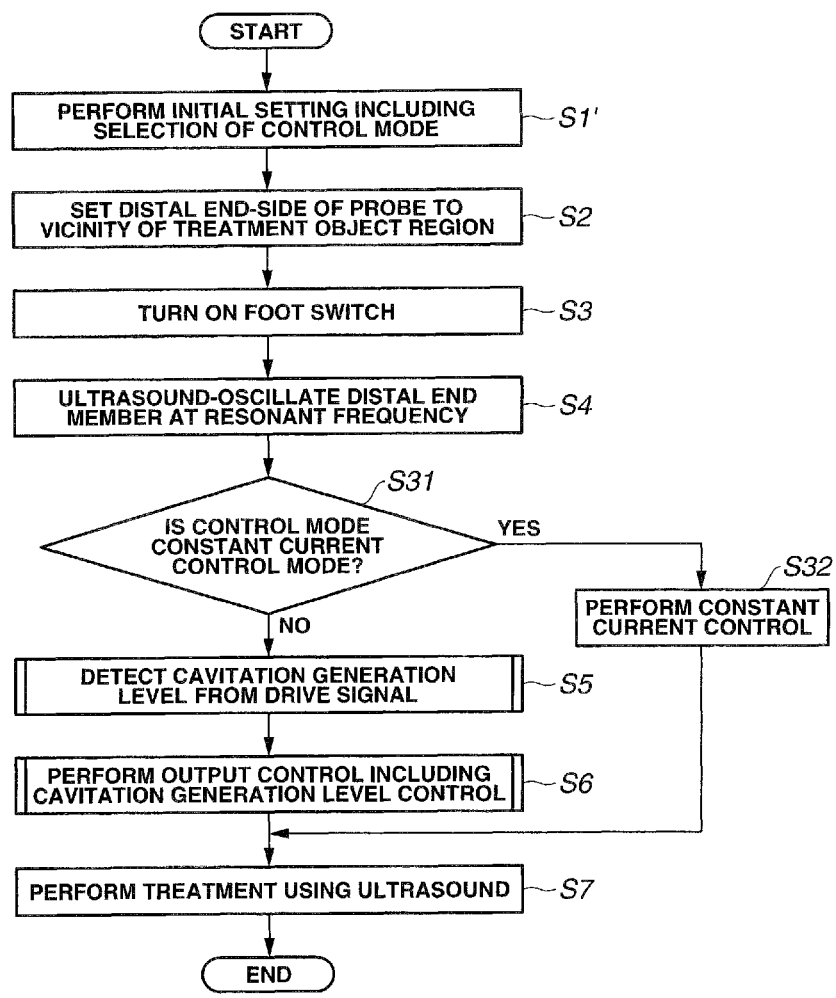
FIG. 12 is a flowchart showing an example of a control method of an ultrasound operation apparatus according to the second embodiment.

Other configurations are the same as those in the first embodiment. A representative example of the control method according to the present embodiment will be described using FIG. 12. Since the present control method is similar to one in the first embodiment, a description will be given with reference to FIG. 6.

First, as shown in step S1', an operator performs initial setting including a selection of a control mode. Then, processing of steps S2 to S4 are performed in the same manner as in FIG. 6. In step S31 subsequent to step S4, the CPU 40 judges whether the control mode is the constant current control mode or not. In the case of the constant current control mode, as shown in step S32, the CPU 40 performs output control (constant current control) corresponding to the setting by the setting section 24C. The routine then proceeds to step S7.

On the other hand, when the result of the judgment in step S31 is not the constant current control mode or, in other words, in the case of the cavitation control mode, the CPU 40 detects the cavitation generation level from an output signal of the filter circuit 39 in the same manner as in step S5 of FIG. 6. Further, in the following step S6, the CPU 40 performs output control of a drive signal by performing cavitation generation level control so as to maintain the level set by the setting section 24C from a detected cavitation level signal Sc.

In step S7 subsequent to step S6, the operator performs ultrasound treatment.

According to the present embodiment, in addition to performing ultrasound treatment under normal constant current control, ultrasound treatment can be performed in a state where the cavitation generation level is automatically controlled.

In addition, the operator can change the control mode in accordance with a handpiece I or a probe Ia to be actually used or with a use condition and perform ultrasound treatment.

Note that, when selecting the cavitation control mode, the CPU 40 may perform control for suppressing cavitation generation by, for example, setting the cavitation level LV1 of the level switch 63a to 0 (LV1=0).

In addition, besides the control method in which constant current control is performed regardless of cavitation generation, the constant current control mode may perform constant current control while suppressing cavitation generation. Furthermore, as indicated by the dashed-two dotted line in FIG. 11, a switch 64 may be provided which, for example, switches between the mode in which constant current control is performed regardless of cavitation generation and the mode in which constant current control is performed while suppressing cavitation generation.

For example, when the switch 64 is turned off, the CPU 40 performs constant current control regardless of cavitation generation. In contrast, when the switch 64 is turned on, the CPU 40 performs constant current control while suppressing cavitation generation.

Next, a first modification of the present embodiment will be described. In the first modification, a control mode can be automatically set in accordance with a handpiece I or a probe Ia to be actually used.

Figure 13:
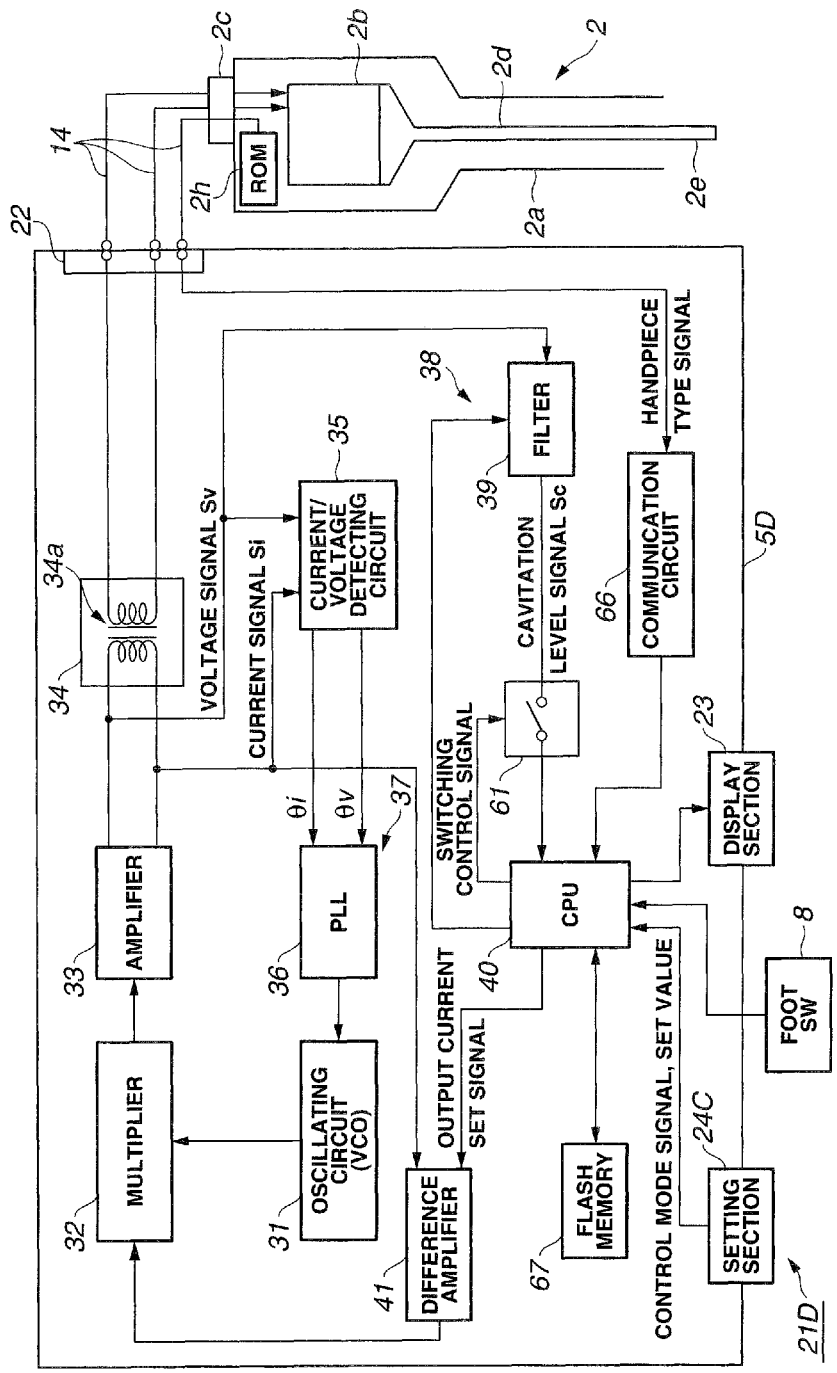
FIG. 13 is a configuration diagram of an ultrasound operation apparatus according to a first modification.

FIG. 13 shows a configuration of an ultrasound operation apparatus 21D according to the first modification. The present modification is provided with an identifying section that identifies a handpiece I as will be described below and is arranged to switch control modes in accordance with an identification result.

The ultrasound operation apparatus 21D is has the same configuration as that of the ultrasound operation apparatus 21C in FIG. 10, except that each of the handpieces I (in FIG. 13, I=2) have, for example, a ROM Ih forming an identifier that generates a handpiece identification information (also simply referred to as an identification signal) built into, for example, a proximal end section of a probe Ia.

In addition, an ultrasound driving apparatus 5D is provided with a communication circuit 66 that reads a handpiece identification signal stored in the ROM Ih from a handpiece I connected to the ultrasound driving apparatus 5D via an ultrasound cable 14. The communication circuit 66 sends a read handpiece identification signal to the CPU 40.

According to the handpiece identification signal from the communication circuit 66, the CPU 40 is capable of identifying a type of a handpiece I, a type of a transducer Ib mounted on the handpiece I, a shape or a state of a distal end section of a probe Ia of the handpiece I, and the like.

In accordance with the handpiece identification signal, the CPU 40 refers to information stored in, for example, a flash memory 67, to automatically select and set either the constant current control mode or the cavitation control mode.

Information on which of the control modes is to be used in correspondence with the handpiece identification signal is stored in advance in the flash memory 67. The information stored in the flash memory 67 can be modified or updated from, for example, the setting section 24C via the CPU 40.

For example, when the handpiece 2 is connected to the ultrasound driving apparatus 5D, the CPU 40 refers to corresponding information to select the constant current control mode. In contrast, when the handpiece 3 is connected to the ultrasound driving apparatus 5D, the CPU 40 refers to corresponding information to select the cavitation control mode.

In addition, when information for manually setting (selecting) the control mode from the setting section 24C is stored in the flash memory 67, the CPU 40 preferentially sets the control mode manually selected by the operator from the setting section 24C.

The present modification is not limited to the example in which respective pieces of handpiece identification information are stored in the ROM Ih. Alternatively, a handpiece serial number or the like may be stored and the type or the like of the handpiece corresponding to the serial number may be identified from the serial number by the CPU 40 with reference to information stored in the flash memory 67.

In addition, the present modification is not limited to the case of the ROM Ih. Alternatively, for example, identification may be performed based on resistance values, or types or the like may be identifiable from arrangements of on/off states of, for example, a dip switch made up of a plurality of switch elements.

Figure 14:
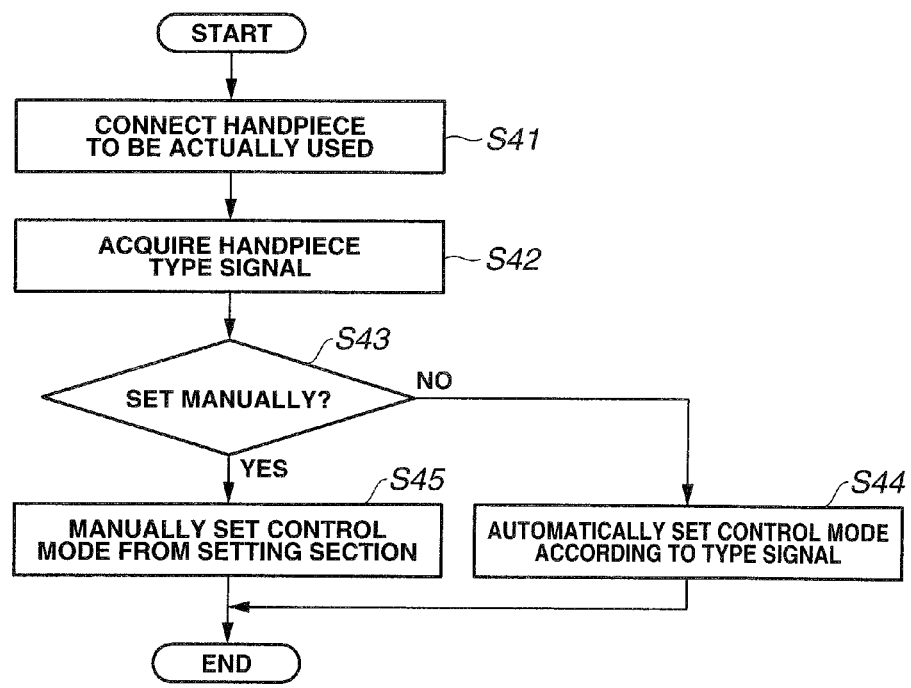
FIG. 14 is a flowchart showing a control method according to the first modification.

Next, operations of the present modification will be described with reference to the flowchart shown in FIG. 14.

As shown in step S41, the operator connects a handpiece I to be actually used to the ultrasound driving apparatus 5D and powers on the same.

Then, as shown in step S42, the CPU 40 acquires a type signal of the handpiece I via the communication circuit 66 from the ROM Ih of the handpiece I. In other words, the CPU 40 identifies the type of the handpiece I.

As shown in a following step S43, the CPU 40 refers to information stored in the flash memory 67 to, for example, judge from the identification signal whether to perform manual setting.

Then, as shown in step S44, in the case where manual setting is not performed or, in other words, in the case of automatic setting, the CPU 40 automatically sets a control mode according to the identification signal. That is, according to the identification result by the identifying section, the CPU 40 automatically selects or automatically switches to one control mode among a plurality of control modes.

In contrast, in the case of manual setting as shown in step S45, the CPU 40 sets a control mode manually selected from the setting section 24C. The control mode setting operation is completed in this manner. Following the control mode setting operation, operations of step S2 shown in FIG. 12 and thereafter are to be performed after, for example, the initial setting.

According to the present modification, by having the operator register in the flash memory 67, in advance, information on control modes to be desirably adopted in correspondence to a type of a handpiece, subsequently, one control mode among a plurality of control modes will be automatically set according to the information. As a result, operability of treatment by the operator can be improved.

In addition, the operator can also manually and preferentially select the constant current control mode or the cavitation control mode using the setting section 24C to perform treatment.

Figure 15:
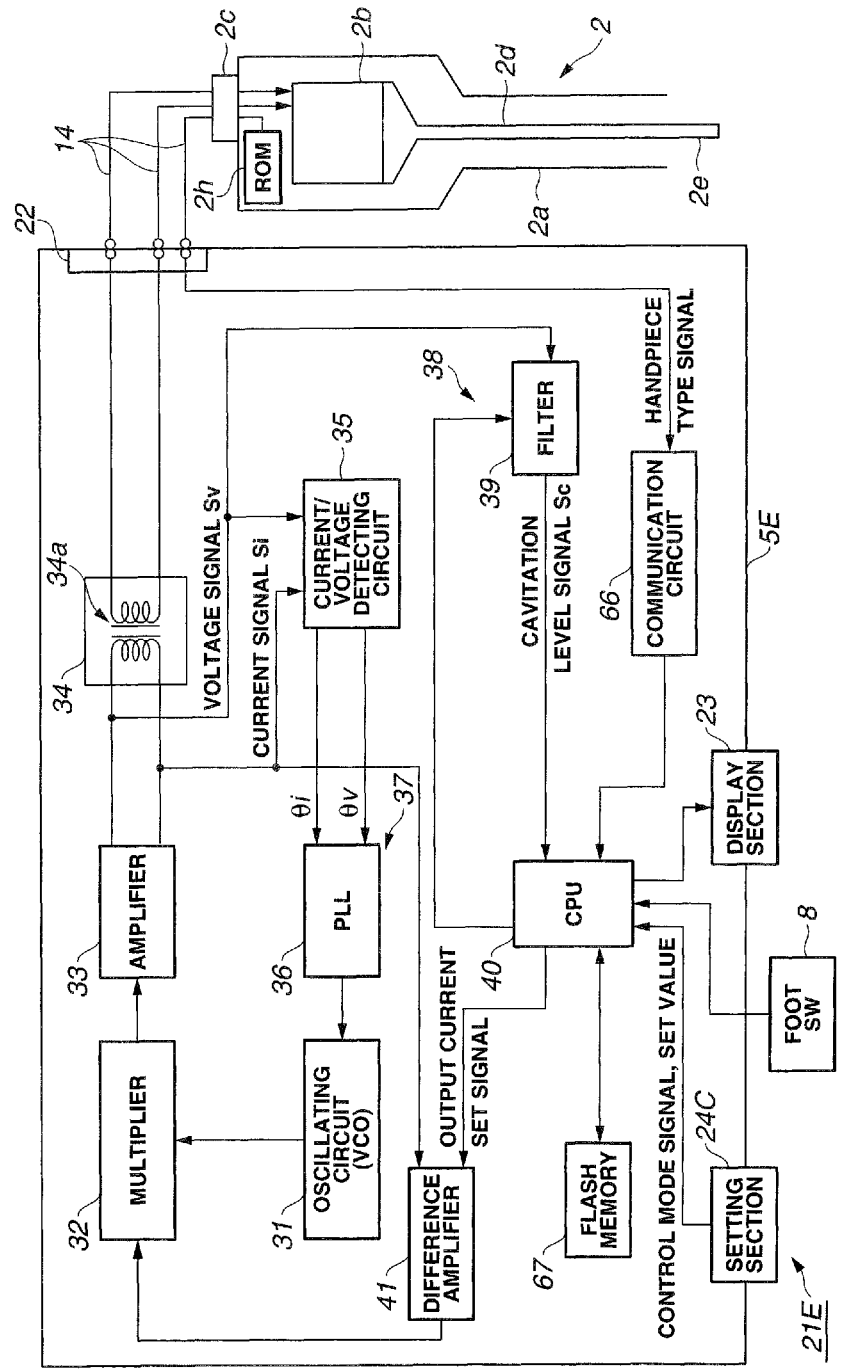
FIG. 15 is a configuration diagram of an ultrasound operation apparatus according to a second modification.

FIG. 15 shows a configuration of an ultrasound operation apparatus 21E according to a second modification.

The ultrasound operation apparatus 21E adopts an ultrasound driving apparatus 5E configured by eliminating the relay apparatus 61 from the ultrasound driving apparatus 5D of the ultrasound operation apparatus 21D shown in FIG. 13. In this case, a cavitation level signal Sc of the filter circuit 39 is inputted to the CPU 40.

The CPU 40 refers to the cavitation level signal Sc in accordance with a control mode set by a handpiece identification signal or a control mode selected (set) with the setting section 24C.

Operations of the present modification are approximately the same as the operations of FIG. 13. As an operation different from the configuration of FIG. 13, in a state where the constant current control mode is set, when an operator changes from the output level at which cavitation is generated to an output level equal to or lower than the output level at which cavitation generation is suspended, the operator can set the output level to the output level at which cavitation generation is suspended with favorable responsiveness by adopting the control described using FIG. 9.

Figure 16:
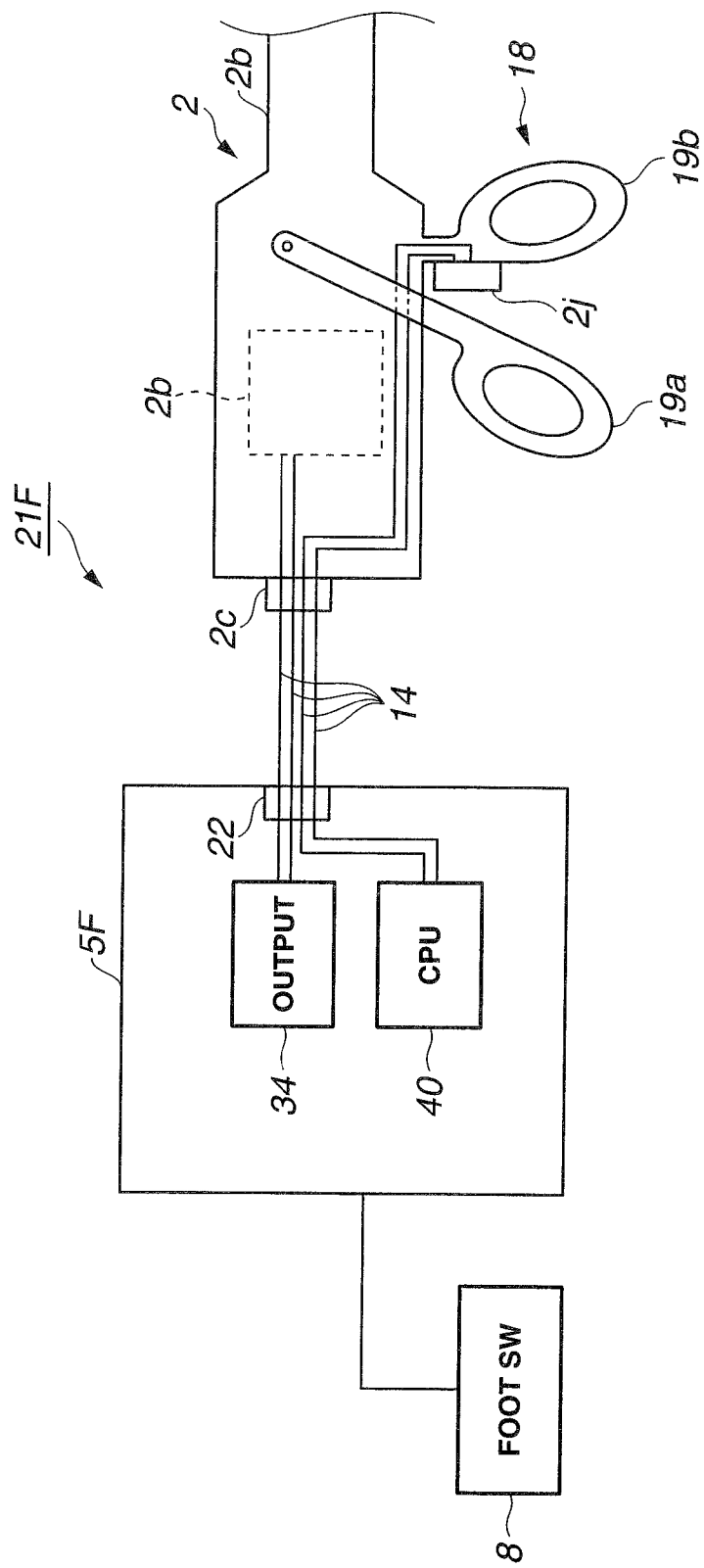
FIG. 16 is a diagram showing an overview of substantial parts of an ultrasound operation apparatus according to a third modification.

FIG. 16 shows a rough configuration of substantial parts of an ultrasound operation apparatus 21F according to a third modification. The present modification enables a variation in a use situation of a specific treatment instrument to be detected to automatically switch control modes.

The ultrasound operation apparatus 21F adopts an ultrasound driving apparatus 5F configured by eliminating the communication circuit 66 from the ultrasound driving apparatus 5E of the ultrasound operation apparatus 21E shown in FIG. 15, in which a detection signal from a sensor 2j provided on a specific handpiece 2 is inputted to the CPU 40.

As shown in FIG. 16, the sensor 2j whose state is changed from off to on by a pressing force is fixed to, for example, a position on a fixed handle 19b of the handpiece 2 which opposes a movable handle 19a.

The sensor 2j is for detecting an open/closed state of the handle 18 and, for example, outputs an on detection signal when the handle 18 is in a closed state and an off detection signal when the handle 18 is in an open state.

Moreover, the distal end members 2e, 2g on the distal end-side of the probe 2a open/close in accordance with an open/closed state of the handle 18. Therefore, the sensor 2j outputs a signal detecting the open/closed state of the distal end section (distal end members 2e, 2g).

The CPU 40 switches control modes in accordance with a detection signal of the sensor 2j that detects the open/closed state of the distal end section based on whether the handle 18 is open/closed. Information for switching control modes in accordance with the detection signal of the sensor 2*j* is stored in the flash memory 67, for example.

Figure 17:
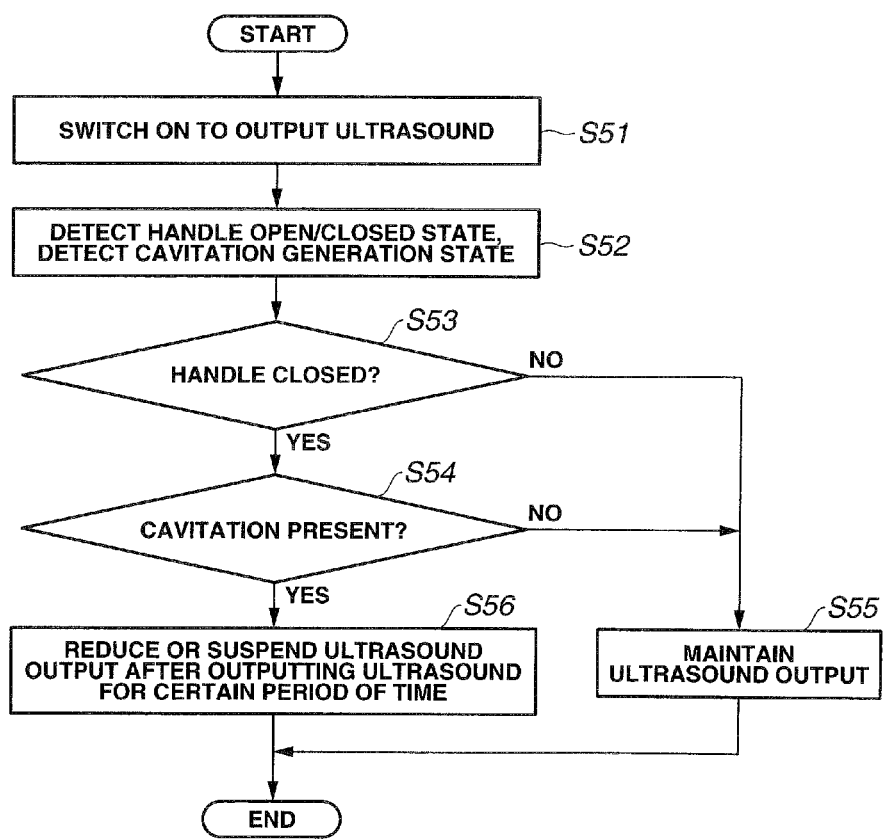
FIG. 17 is a flowchart showing a control method according to the third modification.

FIG. 17 shows a flowchart of operations according to the present modification. After the ultrasound driving apparatus 5F is powered on, when the foot switch 8 is turned on, ultrasound is outputted as shown in step S51.

In other words, a drive signal is applied to the transducer 2*b* to cause the transducer 2*b* to ultrasound-oscillate, whereby the ultrasound oscillation is transmitted to the distal end member 2*e* to cause the distal end member 2*e* to ultrasound-oscillate (hereinafter abbreviated as "output ultrasound").

As shown in step S52, the CPU 40 detects opening/closing of the handle 18 from a detection signal of the sensor 2*j* and a cavitation generation state from an output signal of the filter circuit 39.

Then, in step S53, the CPU 40 judges whether the handle 18 is closed or not. For example, an operator opens the handle 18 (and the distal end section) to perform an exfoliation treatment and closes the handle 18 to perform a coagulation/dissection treatment.

When the handle 18 is closed, the CPU 40 proceeds to step S54, and when the handle 18 is open, the CPU 40 proceeds to step S55.

In step S54, the CPU 40 further judges whether cavitation generation is present (hereinafter abbreviated as cavitation present). In the case of a judgment result of cavitation absent, the routine proceeds to step S55.

In step S55, an immediately-preceding ultrasound output state is maintained. The operator continues ultrasound treatment in the same ultrasound output state.

On the other hand, when the judgment result in step S53 is cavitation present, as shown in step S56, for example, ultrasound output is reduced or suspended after ultrasound is outputted for a certain amount of time.

That is, when the handle 18 is closed, the CPU 40 further judges whether cavitation is generated or not. If cavitation is generated, the CPU 40 suppresses (including output reduction and suspension) cavitation, and if cavitation is not generated, the CPU 40 performs control so as to maintain the ultrasound output in the same output state.

In other words, when the handle 18 is closed and cavitation is present, after a certain amount of time of output, the CPU 40 switches to a control mode for suppressing cavitation generation.

Figure 18:
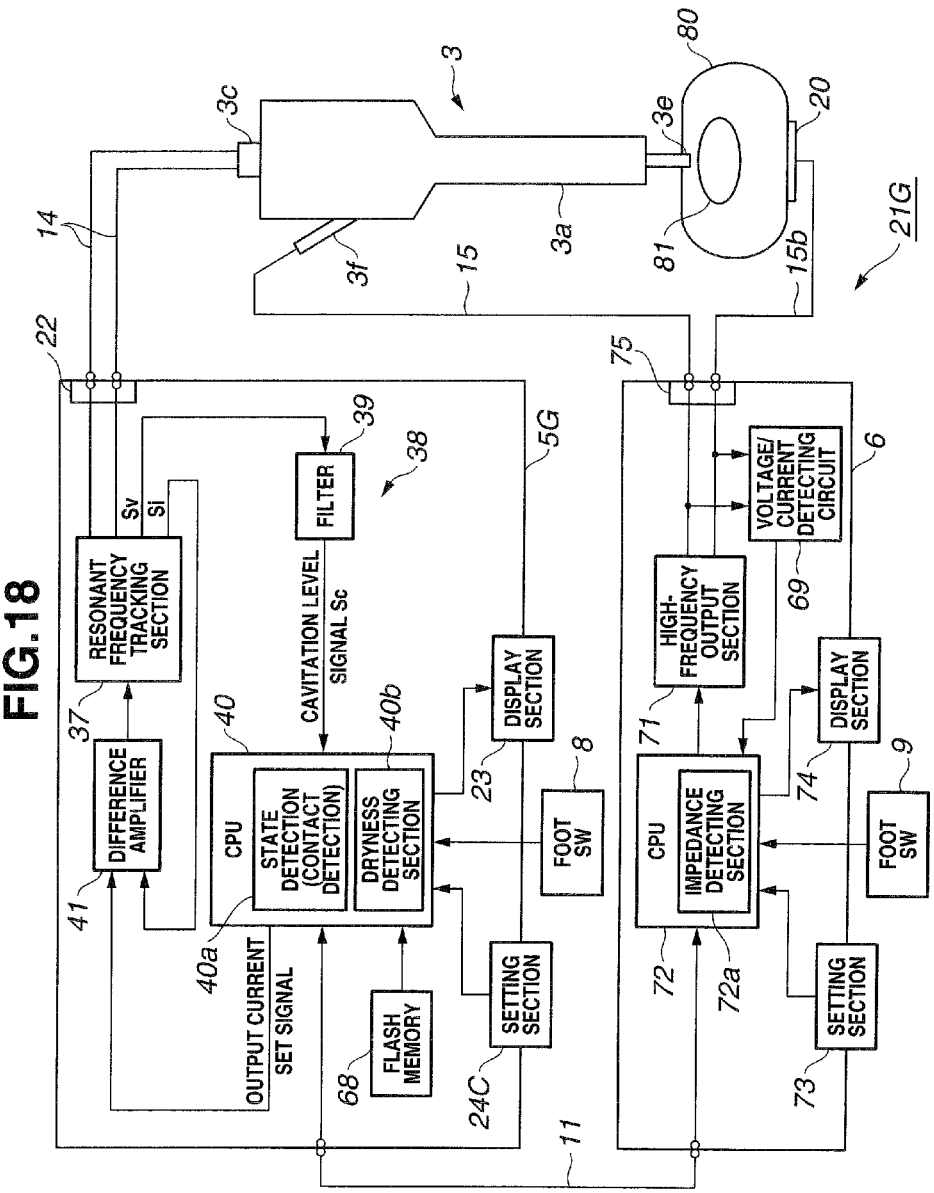
FIG. 18 is a block diagram of a configuration of an ultrasound operation system including a third embodiment of the present invention.

When ultrasound is outputted for a certain amount of time in step S56, for example, a high-frequency impedance of living tissue may be monitored. Moreover, an impedance detecting section for monitoring the high-frequency impedance is shown in FIG. 18, for example.

High-frequency impedance varies when carbonization/degeneration of a living tissue treated by friction caused by ultrasound advances to same extent.

When the monitoring of a state of high-frequency impedance variation reveals that carbonization/degeneration has advanced to same extent and that coagulation treatment has been performed, the ultrasound output may be reduced or suspended.

In contrast, when the judgment in step S53 reveals that the handle 18 is not closed or, in other words, when the handle 18 is open, ultrasound output is maintained as shown in step S55.

As described above, when the handle 18 is open, the CPU 40 performs control so as to maintain ultrasound output in the same output state in both a state where cavitation is generated and a state where cavitation is not generated. In this case, control may be performed so as to generate cavitation.

When performing coagulation/dissection treatment with the distal end members 2*g*, 2*e* in a closed state, an operator desires to perform such treatment while suppressing cavitation in many cases. A control method shown in FIG. 18 facilitates such treatment and improves operability for the operator when performing the treatment.

In addition, there are cases where the operator sets the distal end members 2*e*, 2*g* to an open state to perform exfoliation treatment using only the ultrasound-oscillating distal end member 2*e* without grasping living tissue that is a treatment object. Even in such cases, the operator is capable of continuing treatment while maintaining an output state of ultrasound oscillation.

According to the present modification, output control of a drive signal is changed in accordance with a variation in a use situation of the handpiece 2, so that an operator can be relieved from having to perform an output changing operation in the midst of treatment. In other words, the present modification is capable of improving the operability of an ultrasound operation.

(Third Embodiment)

Next, a third embodiment of the present invention will be described with reference to FIG. 18. The present embodiment uses the detection section for detecting cavitation generation as a state detecting section for detecting a state of living tissue that is a treatment object or a state of the distal end section of a probe Ia.

FIG. 18 shows a configuration of an ultrasound operation apparatus 21G according to the third embodiment of the present invention. The present embodiment is shown as a configuration example that is also provided with the high-frequency output apparatus 6 shown in, for example, FIG. 1.

The ultrasound operation apparatus 21G includes a handpiece 3, an ultrasound driving apparatus 5G, and the high-frequency output apparatus 6. The ultrasound driving apparatus 5G is, configured by eliminating the communication circuit 66 for identifying a handpiece type from the ultrasound driving apparatus 5E shown in FIG. 15. In FIG. 18, circuits from an oscillating circuit 31 to a PLL circuit 36 are represented by a resonant frequency tracking section 37 constituted by the circuits.

A CPU 40 according to the present embodiment includes a function of a state detecting section 40*a* that performs state detection (including state judgment) of a distal end-side of a probe 3*a* from a cavitation level signal Sc, as a physical quantity attributable to cavitation, which is outputted from a filter circuit 39 constituting a detecting section 38.

In other words, the filter circuit 39 that generates a cavitation level signal Sc generates a state detection signal for state detection of the distal end-side of the probe 3*a*.

The state detecting section 40*a* includes a function of a contact detecting section that detects or judges a contact state, that is, whether or not, the distal end section (more specifically, the distal end member 3*e*) of the probe 3*a* is in contact with a moisture-containing living tissue that is a treatment object. Moreover, in the case of metal or the like which does not contain moisture, the state detecting section 40*a* does not have a function for detecting whether the distal end section of the probe 3*a* is in contact with a metal surface or not.

In addition, the CPU 40 includes a function of a dryness detecting section 40*b* that detects, based on a cavitation level signal Sc, a state of dryness of a moisture-containing living tissue.

Living tissue that is a treatment object is dried by an ultrasound (and high-frequency cauterization) treatment, and as drying progresses, the moisture content of the living tissue decreases, resulting in a reduction of the cavitation generation level.

Therefore, it is now possible to detect a state of dryness from a level of a cavitation level signal Sc as a frequency component signal of ultrasound other than a drive frequency of a drive signal.

Figure 21:
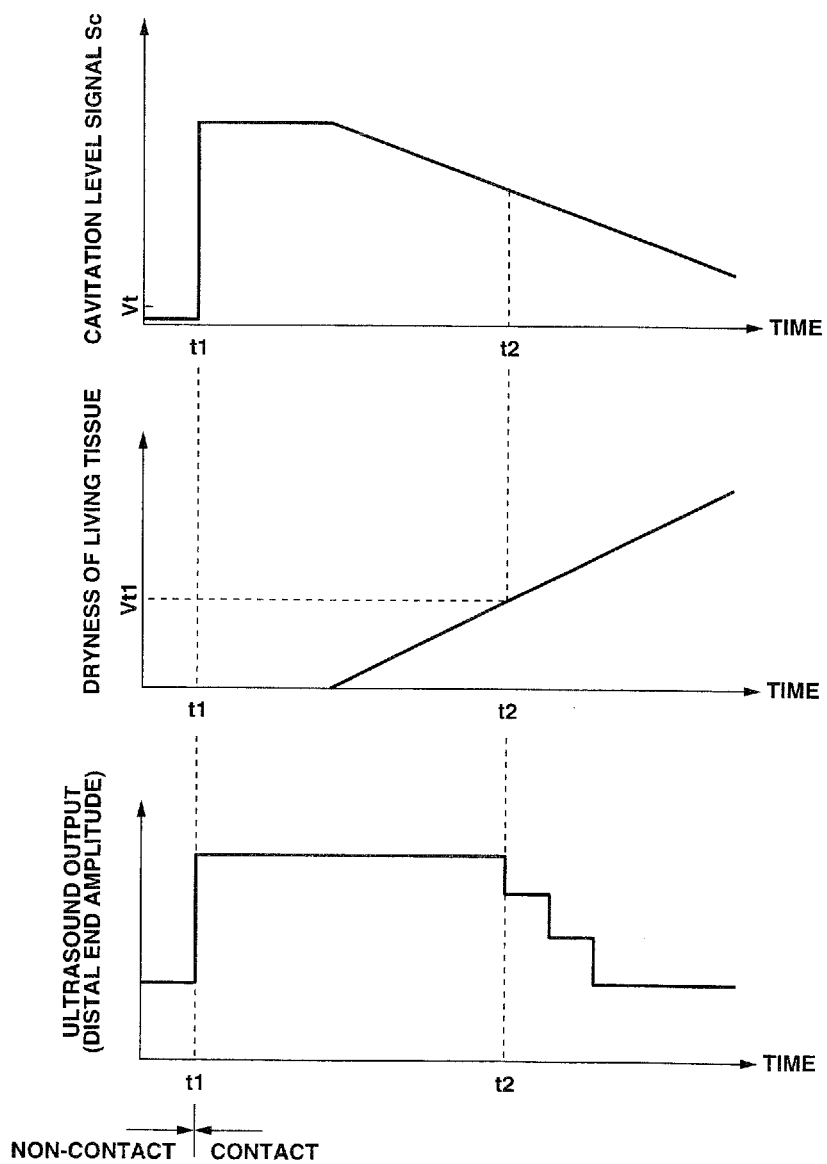
FIG. 21 is an explanatory diagram showing temporal variations in a cavitation level signal and the like when treatment is performed according to the third embodiment.

The dryness detecting section 40b of the CPU 40 detects a state of dryness from a level of the cavitation level signal Sc. Moreover, as shown in FIG. 21, instead of immediately detecting the dryness from the level of the cavitation level signal Sc, the dryness (degree of dryness) is detected from a temporal variation of an initial cavitation level.

The CPU 40 temporally stores detected cavitation level values and dryness information in the flash memory 68, for example. In addition, the CPU 40 refers to temporal information regarding the cavitation level values and the dryness to judge progress of treatment on the living tissue.

Furthermore, the flash memory 68 also stores a control program that varies output control when treatment is carried out by the CPU 40.

Moreover, the high-frequency output apparatus 6 shown in FIG. 5 also includes: a high-frequency output section 71 that outputs a high-frequency output signal; a CPU 72 as a control section that controls operations of the high-frequency output section 71 and the like; a setting section 73 for performing output setting and the like of a high-frequency output signal; and a display section 74 that displays an output value and the like. In addition, a foot switch 9 is connected by a foot switch cable to the CPU 72.

A high-frequency output signal outputted from the high-frequency output section 71 is applied to a high-frequency connector 3f of a handpiece 3 via a high-frequency cable 15 connected to a high-frequency output connector 75. The high-frequency output signal applied to the high-frequency connector 3f is transmitted to the distal end member 3e through an ultrasound transmitting member 3d as a conducting section inside the probe 3a.

In addition, a return electrode 20 is disposed so as to come into contact with a patient 80 over a wide area. A high-frequency current having flown from the distal end member 3e to an organ 81 as living tissue that is a treatment object travels to the return electrode 20 and returns to the high-frequency output apparatus 6 via a return cable 15b connected to the return electrode 20.

The CPU 40 of the ultrasound driving apparatus 5G and the CPU 72 of the high-frequency output apparatus 6 are communicably connected each other by a communication cable 11.

In addition, as will be described below, the CPU 40 controls an output value of an ultrasound drive signal in accordance with a judgment result of a presence/absence of contact, and through communication, controls an output value of a high-frequency output signal via the CPU 72.

More specifically, in a state of a judgment result in which the distal end member 3e of the probe 3a is not in contact with living tissue, the CPU 40 performs control to reduce both ultrasound and high-frequency outputs.

In contrast, in a state of a judgment result in which the distal end member 3e of the probe 3a is in contact with living tissue, the CPU 40 sets both ultrasound and high-frequency outputs to output values for treatment.

In addition, a high-frequency voltage and current supplied from the high-frequency output section 71 to the living tissue are inputted to the CPU 72 via a voltage/current detecting circuit 69. The CPU 72 includes a function of an impedance detecting section 72a that computes voltage/current from the detected voltage and current and which detects a high-frequency impedance value when the living tissue that is a treatment object is assumed to be a load.

The CPU 72 transmits a detected high-frequency impedance value to the CPU 40 via the communication cable 11. The CPU 40 judges carbonization/degeneration of the living tissue that is the treatment object from the transmitted high-frequency impedance value. Alternatively, a result of the judgment by the CPU 72 side may be transmitted to the CPU 40.

Next, operations for performing treatment according to the present embodiment by, for example, bringing the distal end member 3e of the probe 3a into contact with living tissue that is a treatment object such as the organ 81 will be described with reference to FIG. 19.

As shown in FIG. 18, in a state where the handpiece 3 is connected to the ultrasound driving apparatus 5G and the high-frequency output apparatus 6, an operator powers on the ultrasound driving apparatus 5G and the high-frequency output apparatus 6.

Figure 19:
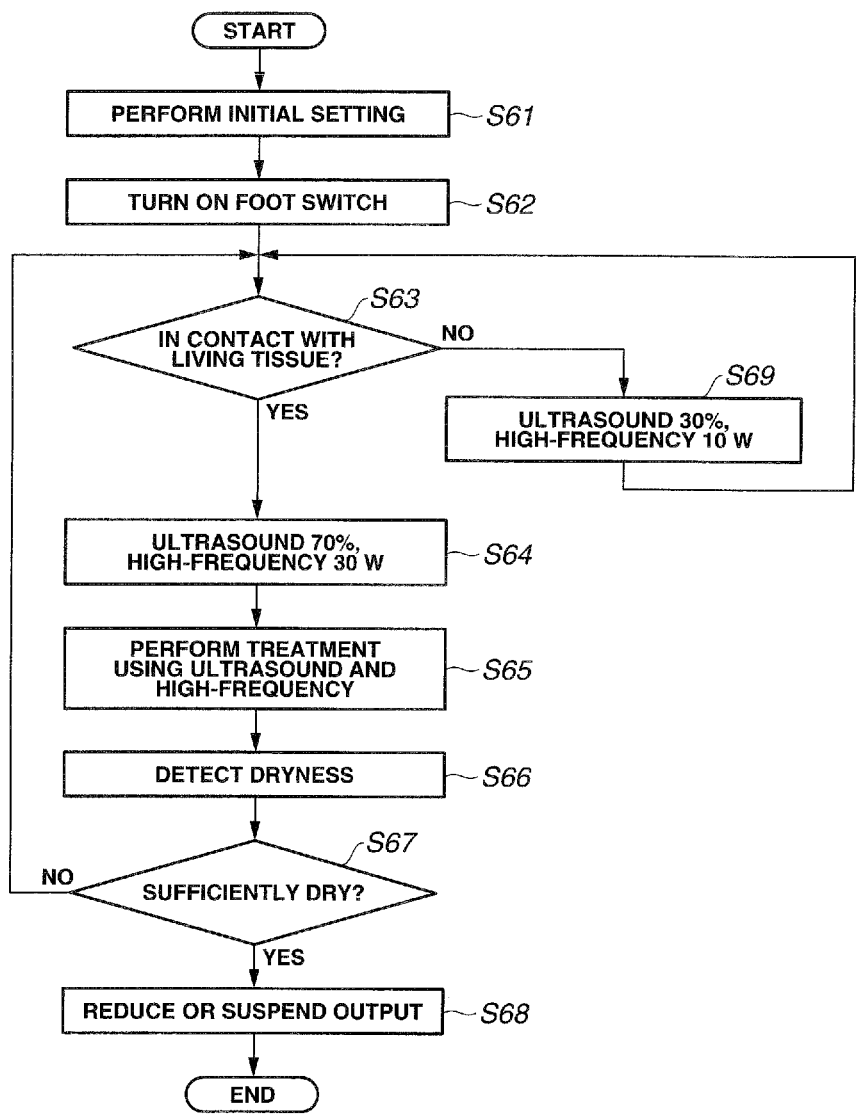
FIG. 19 is a flowchart showing an example of a control method according to the third embodiment.

As shown in FIG. 19, in step S61, the operator performs initial setting. As the initial setting, the operator sets an ultrasound set value and high-frequency output value for performing treatment. In the following example, ultrasound is assumed to be 70% of a maximum set value (hereinafter abbreviated as 70%) and a high-frequency output set value to be 30 W (hereinafter abbreviated as 30 W).

In a next step S62, the operator turns on the foot switches 8 and 9.

Then, in step S63, the CPU 40 judges whether or not the distal end member 3e of the probe 3a is in contact with the living tissue by comparing an inputted cavitation level signal Sc with a threshold Vt approximating 0 (refer to FIG. 21). In other words, the CPU 40 judges that the distal end member 3e is in contact with the living tissue if the cavitation level signal Sc exceeds the threshold Vt, and if it is below the threshold Vt, judges that the distal end member 3e is not in contact with the living tissue.

When it is judged that the distal end member 3e is in contact with the living tissue, as shown in step S64, the CPU 40 performs output control so as to maintain a set value for treatment that was set in the initial setting.

Specifically, the CPU 40 performs output control so that ultrasound is 70% and high-frequency is 30 W (refer to ultrasound output immediately after the time t1 shown in FIG. 21).

Then, as shown in step S65, in an output control state of the set value for treatment, the operator performs treatment on the living tissue using ultrasound and high-frequency.

Furthermore, in this case, in step S66, the CPU 40 detects dryness of a surface of a portion to be treated of the living tissue. The CPU 40 detects (evaluates) a degree of dryness from a level of a cavitation level signal Sc and from a temporal variation of the level.

For example, as shown in FIG. 21, when the cavitation level signal Sc is constant, it is judged that the dryness of the living tissue has not progressed, and when the level of the cavitation level signal Sc declines, it is judged that dryness has progressed and the degree of dryness is detected.

Then, in the following step S67, the CPU 40 compares the detected dryness with a preset dryness threshold and judges whether dryness is sufficient or not.

When it is judged that dryness is sufficient and treatment may be terminated, in step S68, the CPU 40 displays the fact that dryness is sufficient using a display section 23 and reduces or suspends output. To determine whether to reduce or suspend output, a judgment may further be made from a high-frequency impedance value of the living tissue from the impedance detecting section 72a on whether the living tissue is sufficiently carbonized/degenerated or not. Thus, after step S68, the control method shown in FIG. 19 is terminated.

In contrast, in step S67, when the CPU 40 judges that dryness is insufficient, the routine returns to step S63.

In step S63, when the CPU 40 judges that the distal end member 3e is not in contact with the living tissue, the routine moves on to step S69. In step S69, the CPU 40 performs output control so that a set value (output) is smaller than the set value for treatment.

For example, the CPU 40 performs output control so that ultrasound is 30% and high-frequency is 10 W. The routine then returns to step S63.

As described, in the present embodiment, detection is made on whether or not the distal end section of the probe 3a is in contact with living tissue and to control is performed to vary ultrasound and high-frequency outputs in accordance with a result of the judgment. In other words, when the distal end section is in contact with living tissue, the CPU 40 constituting the output control section performs output control so as to maintain the output state suitable for treatment, and when it is not in contact, the CPU 40 performs output control so that a small output state is obtained.

Therefore, according to the present embodiment, when the operator temporarily sets the distal end section of the probe 3a to a non-contact state with the living tissue during treatment, an output state can be automatically reduced without performing an operation to reduce output using the setting section. As a result, operability can be improved.

In addition, since the output state for treatment can be automatically set by bringing the distal end section of the probe 3a into contact with the living tissue from a non-contact state, operability can be improved.

Though the output control method shown in FIG. 19 has been described using the example in which ultrasound output is maintained at a certain value when the distal end section of the probe 3a is brought into contact with the living tissue, ultrasound output may be varied in accordance with the dryness. An output control method of such a case is partially shown in FIG. 20.

Figure 20:
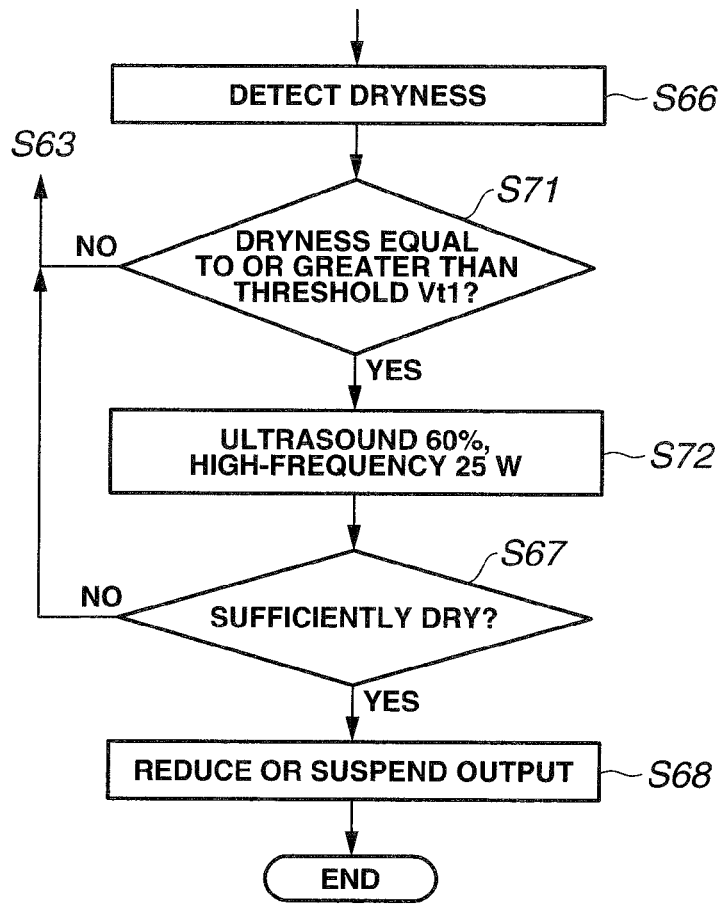
FIG. 20 is a flowchart showing a portion of processing changed from FIG. 19.

In FIG. 20, steps S71 and S72 are added between steps S66 and S67 shown in FIG. 19.

In step S71 following step S66, the CPU 40 judges whether or not the detected dryness is equal to or greater than (the dryness of) a preset threshold Vt1. When dryness is less than the threshold Vt1, the routine returns to step S63.

In contrast, when dryness is equal to or greater than the threshold Vt1, in step S72, the CPU 40 performs output control so that the output becomes lower by a predetermined amount than the set value for treatment that was set in the initial setting.

Specifically, the CPU 40 performs output control so that ultrasound is 60% and high-frequency is 25 W.

In the following step S67, the CPU 40 judges whether or not dryness is sufficiently high to reach a value even higher than the threshold Vt1. Processings subsequent to the judgment is the same as those shown in FIG. 18. Though FIG. 20 shows a case where output is reduced by a predetermined amount in accordance with a result of judgment with the threshold Vt1 in step S71, output may be reduced at a plurality of stages by setting a plurality of thresholds.

FIG. 21 shows examples of temporal variations in the cavitation level signal Sc, dryness, and ultrasound output in accordance with such output control.

In FIG. 21 shows a case where the distal end section of the probe 2a is brought into contact with living tissue from a non-contact state at the time t1.

The distal end section of the probe 2a is not in contact with the living tissue during a period until immediately before the time t1. Therefore, since the cavitation level signal Sc is virtually 0, that is, equal to or lower than a threshold Vt, the CPU 40 makes a judgment of non-contact. In addition, ultrasound output is controlled by the CPU 40 so as to be a value lower than the initial set value.

When the distal end section of the probe 2a comes into contact with the living tissue at the time t1, the cavitation level signal Sc increases. The CPU 40 makes a judgment of contact when the cavitation level signal Sc exceeds the threshold Vt. In addition, ultrasound output is controlled by the CPU 40 so as to be the initial set value, in other words, the set value for treatment.

Treatment on the living tissue is performed using ultrasound output at the initial set value. Since the moisture content of the living tissue decreases as the treatment progresses, as shown in FIG. 21, the cavitation level signal Sc decreases and the decrease is detected as the dryness of the living tissue. In other words, the dryness of the living tissue increases as the cavitation level signal Sc decreases.

Then, for example, at the time t2 at which the dryness equals or exceeds the threshold Vt1, ultrasound output is reduced by the CPU 40 by a predetermined amount. Treatment on the living tissue is performed in this manner.

The treatment is terminated when the treatment has progressed to a state where the living tissue is sufficiently dry.

According to the present embodiment, by detecting whether or not the distal end section of the probe 3a is in contact with living tissue, ultrasound output can be varied in accordance with the result of the detection.

Therefore, according to the present embodiment, operability for the operator when performing treatment can be improved. In addition, by detecting dryness due to the treatment of the living tissue, the operator can be presented with an environment that facilitates smoother treatment.

Note that, different embodiments may be constructed by partially combining the embodiments and the like described above.

In addition, the cavitation control method for controlling a cavitation generation level may be formed using the ultrasound operation control methods according to the embodiments described above. For example, the cavitation control method may be formed using the ultrasound operation control method shown in FIGS. 6 and 7.

Having described the preferred embodiments of the invention referring to the accompanying drawings, it should be understood that the present invention is not limited to those precise embodiments and various changes and modifications thereof could be made by one skilled in the art without departing from the spirit or scope of the invention as defined in the appended claims.

What is claimed is:

1. An ultrasound operation apparatus for treating a living tissue, the apparatus comprising:
   an ultrasound transducer configured to generate ultrasound oscillation;
   a probe having a proximal end section operatively coupled to the ultrasound transducer and a distal end section that generates ultrasound oscillation, the probe being configured to transmit the ultrasound oscillation generated by the ultrasound transducer from the proximal end section to the distal end section;
   a resonant frequency tracking section configured to automatically adjust a frequency of a drive signal so as to track a resonant frequency of the ultrasound transducer and cause the distal end section to ultrasound-oscillate at the resonant frequency;

a setting section configured to allow an operator to set a value as a target level of a cavitation to be generated during treatment of the living tissue;

a detecting section configured to detect a generation level of the cavitation by detecting a signal level of a frequency component signal obtained by integrating the drive signal in a predetermined frequency band excluding the resonant frequency; and a control section configured to compare the generation level of the cavitation which is detected by the detecting section with the target level set by the setting section, and perform control so as to vary an output of the drive signal such that the generation level is at the target level;

wherein the detecting section includes a state detecting section that detects a state of dryness of a tissue to be treated or a contact state between the tissue to be treated and the distal end section by detecting the frequency component signal.

2. The ultrasound operation apparatus according to claim 1, wherein the detecting section detects at least one of a voltage value, a current value, and an impedance value in a predetermined frequency band excluding a resonant frequency of the drive signal.

3. The ultrasound operation apparatus according to claim 1, wherein the detecting section includes a filter section that extracts a signal in a predetermined frequency band excluding the resonant frequency of the drive signal, and wherein the detecting section detects the frequency component signal based on the signal extracted by the filter section.

4. The ultrasound operation apparatus according to claim 1, wherein the predetermined frequency band includes a frequency of a divisor of the resonant frequency.

5. The ultrasound operation apparatus according to claim 1, wherein the predetermined frequency band is greater than the resonant frequency and smaller than a second harmonic of the resonant frequency.

6. The ultrasound operation apparatus according to claim 1, wherein the predetermined frequency band is of at least one of a frequency band ranging from 5% to 95% of the resonant frequency or a frequency band ranging from 105% to 195% of the resonant frequency.

7. The ultrasound operation apparatus according to claim 1, wherein the control section switches among a plurality of control modes having different control contents and sets the switched control mode, the control modes varying the drive signal.

8. The ultrasound operation apparatus according to claim 1, wherein the control section identifies a type of the probe or the ultrasound transducer, or a shape or a state of the distal end section, and switches the control modes which vary the drive signal, in accordance with a result of the identification.

9. A cavitation control method for treating a living tissue, the method comprising:

a step of setting by an operator a value as a target level of a cavitation to be generated during treatment of the living tissue;

a step of generating ultrasound oscillation using an ultrasound transducer;

a step of the ultrasound transducer transmitting the ultrasound oscillation to a probe having a proximal end section operatively coupled to the ultrasound transducer and a distal end section that generates ultrasound oscillation;

a step of causing the distal end section to ultrasound-oscillate at a resonant frequency of the ultrasound transducer by automatically adjusting a frequency of a drive signal so as to track the resonant frequency of the ultrasound transducer;

a step of detecting a generation level of the cavitation by detecting a signal level of a frequency component signal obtained by integrating the drive signal in a predetermined frequency band excluding the resonant frequency; and a step of comparing the generation level of the cavitation which is detected by the detecting step with the target level set by the operator, and controlling an output of the drive signal such that the generation level is at the target level;

wherein the detecting step includes a state detecting step that detects a state of dryness of a tissue to be treated or a contact state between the tissue to be treated and the distal end section by detecting the frequency component signal.

10. The cavitation control method according to claim 9, further comprising:

a step of identifying a type of the probe or the ultrasound transducer, or a shape or a state of the distal end section, and switching among a plurality of cavitation control modes in accordance with a result in the identification.

11. The cavitaion control method according to claim 9, wherein the step of detecting the signal level of the frequency component signal is formed by a step for detecting a state of a tissue to be treated or a state of the distal end section.

* * * * *